United States Patent
Saun et al.

(10) Patent No.: US 11,568,542 B2
(45) Date of Patent: Jan. 31, 2023

(54) BODY-MOUNTED OR OBJECT-MOUNTED CAMERA SYSTEM

(71) Applicant: SURGICAL SAFETY TECHNOLOGIES INC., Toronto (CA)

(72) Inventors: Tomas Jaan Saun, Toronto (CA); Teodor Pantchev Grantcharov, Stouffville (CA); Amar S. Chaudhry, Toronto (CA); Juliana De La Vega Fernandez, Toronto (CA)

(73) Assignee: SURGICAL SAFETY TECHNOLOGIES INC., Toronto (CA)

( * ) Notice: Subject to any disclaimer, the term of this patent is extended or adjusted under 35 U.S.C. 154(b) by 189 days.

(21) Appl. No.: 16/859,691

(22) Filed: Apr. 27, 2020

(65) Prior Publication Data

US 2020/0337776 A1     Oct. 29, 2020

Related U.S. Application Data

(60) Provisional application No. 62/838,699, filed on Apr. 25, 2019.

(51) Int. Cl.
*G06T 7/10*        (2017.01)
*A61B 34/10*      (2016.01)
*G06T 1/60*        (2006.01)
*G06T 1/20*        (2006.01)

(52) U.S. Cl.
CPC ............... *G06T 7/10* (2017.01); *A61B 34/10* (2016.02); *G06T 1/20* (2013.01); *G06T 1/60* (2013.01)

(58) Field of Classification Search
CPC ............... G06T 1/20; G06T 1/60; G06T 7/10
See application file for complete search history.

(56) References Cited

U.S. PATENT DOCUMENTS

| | | | |
|---|---|---|---|
| 2016/0260220 A1* | 9/2016 | Liu | A61B 6/488 |
| 2016/0364882 A1* | 12/2016 | Sasagawa | G06V 10/60 |
| 2019/0209080 A1* | 7/2019 | Gullotti | A61B 90/90 |
| 2020/0129780 A1* | 4/2020 | Lachaine | A61N 5/1037 |

OTHER PUBLICATIONS

Liang et al. Fused Video Stabilization on the Pixel 2 and Pixel 2 X. Nov. 10, 2017.
Wang et al. Deep Online Video Stabilization. Feb. 22, 2018.
Long et al. Fully Convolutional Networks for Semantic Segmentation. Mar. 8, 2015.

(Continued)

*Primary Examiner* — Michelle L Sams
(74) *Attorney, Agent, or Firm* — Norton Rose Fulbright Canada LLP

(57) ABSTRACT

An object or body-mounted camera apparatus for recording surgery is provided that is adapted for tracking a relevant visual field of an on-going operation. To help maintain visibility and/or focus of the visual field, specific machine learning approaches are proposed in combination with control commands to shift a physical positioning or a perspective of the camera apparatus. Additional variations are directed to tracking obstructions based on the visual field of the camera, which can be utilized for determining a primary recording for use when there are multiple cameras being used in concert.

20 Claims, 30 Drawing Sheets

(56) References Cited

OTHER PUBLICATIONS

Mittal et al. No-Reference Image Quality Assessment in the Spatial Domain. IEEE Transactions on Image Processing, vol. 21, No. 12, Dec. 2012.
Ren et al. Faster R-CNN: Towards Real-Time Object Detection with Region Proposal Networks. Jan. 6, 2016.
Shahid et al. Applications of artificial neural networks in health care organizational decision-making: A scoping review. Health Economics and Technology Assessment (THETA) Collaborative, University Health Network, Toronto, Canada. Oct. 4, 2018.
Tajbakhsh et al. Convolutional Neural Networks for Medical Image Analysis: Full Training or Fine Tuning? Jun. 2, 2017.

\* cited by examiner

BODY-MOUNTED OR OBJECT-MOUNTED CAMERA SYSTEM

CROSS-REFERENCE

This application claims all benefit, including priority to, and is a non-provisional of U.S. Application No. 62/838,699, entitled "BODY-MOUNTED CAMERA SYSTEM", filed 25 Apr. 2019, incorporated herein by reference in its entirety.

FIELD

The present disclosure generally relates to the field of surgical procedures, an in particular to an object or body-mounted camera system for recording aspects relevant to a surgical procedure.

INTRODUCTION

Embodiments described herein relate to the field of recording surgical procedures. It is challenging for a medical professional performing a procedure to film the medical procedure or surgery. If another person is filming the procedure, then there is an extra body taking space around the operating table, and an increase in personnel cost. Additional personnel in the operating room may disrupt routine workflow and lead to increased operative time, medical errors, and an increased risk of surgical site infection.

Having a simple overhead view, or even a filming by another person may result in part of the procedure being blocked by the head of the person performing the procedure. A head set mount may strain the neck of the operator and have been found to not be stable.

Obstructions are prevalent in surgical procedures, and prior approaches using fixed perspective cameras are deficient.

SUMMARY

As noted above, recording surgical procedures is difficult to accurately accomplish due to practical implementation issues that arise from the innate complexity of the surgical environment during the surgical procedures. Applicants have developed an industry leading operating room "black box" that utilizes, among other inputs, recordings of surgical procedures for automatic (or semi-automatic) collation, review, annotation, or generation of derivative insights.

Prior approaches to recording, such as mounting off the shelf action cameras on fixed stands, or using overhead cameras have been limited in their usefulness as their views are static and prone to being out of focus or obstructed. The quality of recording can be impacted by differences in lighting. High shutter speeds, for example, can be negatively impacted by bright overhead operating room lights.

For use in automated or semi-automated (e.g., human augmented analysis), high recording quality, an ability to maintain focus on key regions of interest (e.g., by shifting focal length or by moving the camera), and an ability to reduce overall bandwidth requirements by enabling compression (e.g., by removing aspects outside of the region of interest) can be useful. Reduced bandwidth is particularly important in some situations as there can be privacy-related challenges specifically in relation to audio-visual data, and the audio-visual data may require enhanced encryption or obfuscation applied prior to transmission. Accordingly, the smaller the bandwidth requirement, the less computationally intensive the encryption or obfuscation needs to be. This is further complicated by facility-specific guidelines that must be adhered to from a privacy perspective.

Other factors for consideration include a need for ergonomic comfort, and an ability to operate in a sterile environment, such as an operating theatre.

As described in some embodiments, an improved approach for recording surgical procedures is proposed. Applicants have tested numerous prototypes and approaches and discuss experimental results and analyses relative to other solutions.

Machine learning approaches are utilized to improve the technical quality of recording outputs, or to annotate recording outputs in respect of an amount of obstruction, etc. In some embodiments, multiple recording devices can be utilized together, such that quality (e.g., as measured by amount of obstruction) can be tracked to modify how the recordings are ultimately processed (e.g., a decision as to which feeds are sent or which feeds are processed). The machine learning approaches, as described in various embodiments below, can also be used to automatically shift aspects of the recording device, such as controlling or requesting moving the recording device in various directions, modifying brightness/contrast settings, changing a focal length, among others.

A recording device can include, for example, an optical instrument, such as camera. The camera can include various apertures that allow light to fall upon a light sensitive sensor, which is then recorded and transformed into an image frame of a stream of frames, which, for example, could comprise a video when played in sequence.

Recording devices are especially useful for surgical procedures, such as open surgeries, laparoscopic surgeries, consultations, examinations, among others, as they provide a mechanism for providing in-procedure feedback or valuable analytics that can be used for improving downstream surgical outcomes. Recording devices can be mounted on various objects. As described herein, variants are provided in respect of wearable cameras, cameras mounted into moveable objects (e.g., an overhead operating room light or armature having a handle for manipulation), mounted onto housing bases (e.g., a ball and socket mount), on tracks allowing movement in one or more directions, among others. The cameras can be, for example, be mounted on a shoulder of a surgeon or other practitioner using a suitable harness.

The recording devices can form a system of devices as the devices can operate in concert to obtain recordings at different perspectives and views of the surgery. This is especially useful in the context of open surgery, where there are many potential obstructions from instruments, hands, bodies, and body parts (e.g., skin flaps, bones). Obtaining unobstructed, stable images is of further importance where the images and recordings are automatically processed by downstream systems.

Low quality or obstructed recordings could lead to incorrect machine-generated predictions and analyses, which may then lead to less useful or less reliable machine generated outputs (e.g., automatic estimation of best-practice procedural characteristics that led to improved surgical outcomes).

Downstream processing of recordings can be utilized, for example, to allow for an improved ambit of computer-generated estimates of potential approaches to improve healthcare outcomes. An example automatically generated output could be that from analyzing the recordings, a particular spacing of sutures during the closing of the wound allows for reduced amount of post-operative care (e.g., and such approach should be more widely adopted). The recordings may be compressed, de-identified, and otherwise provisioned for downstream analysis (e.g., by a secure machine learning server that is kept on-premises to enhance patient privacy). In another embodiment, privacy-enhanced data can be securely transmitted for cloud-based analysis (e.g., to take advantage of additional cloud resources). In another embodiment, federated learning models are used to train models while reducing privacy concerns.

A technical challenge that arises with processing recordings is that the recordings, if taken from a stationary position or perspective, can be of very low value or quality. Premises in which surgical procedures are taking place are often very busy, with multiple practitioners moving around the field of view, and instruments, hands, etc. providing visual obstructions.

Furthermore, the specific area of interest, such as a visual region of interest (e.g., focused on the surgical field) may not have a stable position in the field of view of the camera, especially if the camera is mounted on a dynamically movable object, such as a shoulder mounted camera or an overhead light mounted camera. In the context of a shoulder mounted camera, this is particularly challenging as the mounting point constantly changes positioning and perspective as the surgeon is manipulating instruments with his or her arms.

As described herein, the recording device includes an imaging sensor residing within a housing. There can be multiple recording devices operating in concert. Recording devices can be optical recording devices, such as cameras, and specific approaches to control are described herein.

The recording devices can be wearables (e.g., worn on a harness, on a shoulder, head-mounted), stationary devices (e.g., overhead camera or mounted on a fixed position, such as on a laptop), or user-movable devices, such as an operating room light having a handle from which a surgeon is able to move the light in response to various instructions.

Each recording device can be coupled to a computer processor that can be used in conjunction with computer memory, the computer processor configured to receive the stream of image frames from the imaging sensor and to generate control signals to request the repositioning or movement of the imaging sensor or housing such that a field of view is continuously maintained over the visual region of interest. The computer processor can be in the housing, or coupled to the housing as an external computing device.

A specific machine learning approach is described where a trained machine learning data model architecture continually processes the stream of image frames to continuously identify the visual region of interest to tracking a physical object relating to the surgical procedure in the field of view. For example, the physical object and the corresponding visual region of interest could include a centroid or a center point, which can then be used to generate a displacement vector data structure when the centroid of the visual region of interest has been displaced between temporally proximate frames of the stream of image frames. The physical object may be maintained in the visual region. However, in the example of the shoulder mounted camera, the camera's positioning and angle may shift as the practitioner moves around (e.g., rotates, bends over, shifts shoulder positioning). Accordingly, it is important in some aspects to be able to maintain the region of interest within the visual field of view of the imaging sensor (or to reduce vibrations).

The region of interest can be, for example, identified through a bounding box, which then has a geometric centrepoint. This can be repeated for temporally distant frames, such as sequential frames, and thus there are two positions established in a co-ordinate plane (e.g., a 2 dimensional plane) to establish a displacement vector, which can be stored in a displacement vector data structure (e.g., a tuple of points stored as data values on a data object, such as an array or as variables within an object or class).

The displacement vector data structure is representative of a directional shift, and can include, for example, directional-based coordinates indicating an amplitude and/or a direction of the shift. The processor then generates a control signal requesting movement of the imaging sensor or the housing in a direction based at least on the displacement vector data structure. For example, the processor can then determine the magnitude of the displacement vector (which is the square root of the change in the x coordinate squared+the change in the y coordinate squared), and translated into into 3D motor commands (e.g., activate yaw motor by X amount, activate pitch motor by Y amount). The translations can, for example, be conducted through the imposition of transformation matrices and Jacobian matrices to help fixate the region of interest over the object of interest.

The conversion can include a coordinate transformation based on the the degrees of freedom the imaging sensor and/or the housing is known to be able to operate in. There can be a combination of rotation and translation, and the vectors can be transformed, for example, through the determination of corresponding transformation matrices. A feedback loop can be utilized to reduce an overall error in relation to comparing sent movement instructions to future frames (e.g., did the motor actuation actually reduce error or did error increase?). For example, a PID controller, a PI, or a P controller may be utilized in this aspect.

The control commands can be translated into commands for a human to actuate (e.g., move housing left, move housing right), or translated into machine process-able commands for movement of aspects of the camera or housing itself (e.g., actuate motor to rotate camera, increase/decrease aperture, move housing along a track).

In some embodiments, the object being tracked can be modified through a received command from a surgeon or downstream computing device. For example, a surgeon may provide a command input (e.g., voice input through a microphone or a text input through a keyboard) that changes the physical object being tracked. The recording device then tracks the alternate object and can control operating aspects to maintain focus on the new object being tracked. For example, instead of tracking an open incision area, it may be adapted to track a particular instrument, or a particular object being moved around in the region of interest (e.g., tracking an organ that is being temporarily displaced to allow for access to an underlying area for surgery). For example, one recording device may be tuned to track a particular instrument to ensure that it is not accidentally left behind in the patient.

In another embodiment, instrument tracking can be useful in downstream recording processing to assess whether an instrument was used (and whether it needs to be cleaned and/or disposed of). In another embodiment, instrument tracking can be used to track instrument usage from a cost/insurance perspective such that inventory management systems can properly allocate costs from a budgeting perspective.

In some embodiments, the trained machine learning data model architecture can be a Mask Region-based Convolutional Neural Network (Mask R-CNN) that is adapted for detection of the object and instance segmentation. Other types of neural networks are possible and Mask R-CNNs are provided only as a specific example for illustrative purposes.

The Mask R-CNN can be adapted to predict, for each pixel of an image frame of the stream of frames, a corresponding segmentation mask selected from a plurality of potential segmentation masks, and wherein the visual region of interest is derived at least from the associated segmentation mask corresponding to each pixel. Segmentation masks are useful, especially where there are obstructions.

For example, the plurality of potential segmentation masks can include a first segmentation mask tracking the physical object relating to the surgical procedure in the field of view and one or more additional segmentation masks tracking one or more corresponding obstructions; and the Mask R-CNN can be adapted to utilize the first segmentation mask and the one or more additional segmentation masks together to identify an overall obstruction amount for a particular frame of the stream of frames. The processor can further annotate the stream of image frames with additional metadata indicative of the overall obstruction amount for each frame of the stream of image frames.

In a variant embodiment, the Mask R-CNN is pre-trained on a large scale object detection, segmentation, and captioning data set such that the Mask R-CNN is initialized with weights derived from the pre-training to apply transfer learning where training on previously learned tasks is used to enhance learning of a similar but different task. Training parameters for the Mask-RCNN can, for example, include a decreasing stepwise learning rate as training progresses through staged epochs.

The visual region of interest can, in some instances, be used to crop the stream of image frames, and wherein the computer processor is further configured to store a cropped stream of image frames onto a data storage. This cropping can provide for an improved focus by a reviewer or a downstream machine learning mechanism (e.g., a bleeding predictor mechanism).

In a first embodiment, the housing is mounted on or positioned proximate to an individual's shoulder, and the housing can include or be coupled with a gimbal having actuators thereon for controlling a gimbal roll axis, a gimbal pitch axis and a gimbal yaw axis, as well as a gimbal motor. The displacement vector data structure can be transformed into a corrective gimbal actuator command for physically repositioning the imaging sensor or the housing.

In another variant, the control signal is converted into a user interface output requesting an individual physically reposition the imaging sensor or the housing in accordance with the displacement vector data structure representative of the directional shift. For example, this user interface output can be an onscreen message, a voice prompt, etc., and can include feedback aspects based on the corrected positioning from the displacement vector (e.g., a voice prompt indicating "please move the housing to the right and upwards", "you have moved it too far, please move to the left again"). For example, the recording device is mounted into or positioned proximate to a repositionable overhead light.

Other variations are possible, for example, a chest mounted camera for a surgeon, an overhead camera that can be repositioned or whose angle can be modified, or a camera that is positioned on an existing instrument or coupled to a laptop or smart device. When the camera is mounted on a human, for example, it can be provided as a harness configured to be used with a sterile surgical gown, a camera mounted on a gimbal, a control unit coupled to the camera, and an apparatus mount coupled at one end to the harness and coupled at the other end to the control unit.

The recording device described in various embodiments can be utilized for various applications, including integration into a video capturing system for open surgery (individually or in combination with endoscopic surgery recordings). The recordings can be utilized for remote monitoring/tele-monitoring, or downstream processing for predictive analysis and assessment. Where many recordings are utilized in concert for a particular operation, the segmentation mask analysis can be utilized to identify which of the recordings were of particularly high quality or low quality (e.g., measured by proxy of percentage of frame obstructed at a particular timeframe or particular duration).

The identification of quality can, for example, be then used to determine which recordings to be compressed and transmitted over the network, or in some embodiments, which recordings are to be processed when generating an output for a human reviewer or a downstream analysis mechanism. When generating output for a human reviewer, such as an annotated media file for playback on a graphical user interface, the display device can be adapted to emphasize display (e.g., play on the largest screen) the recording from the recording device for that segment or duration that has the highest quality score (e.g., least obstructed).

This is useful, for example, when there are multiple sources of recordings (e.g., overhead operating room camera, shoulder mounted camera on each surgeon, fixed overhead camera). Accordingly, even during a particularly intensive surgery where surgeons are moving around the operating theatre conducting various tasks, there may be least be one recording of sufficient quality to be stitched together to provide a high quality overall recording of the procedure in the event of review to determine lessons learned, causation, or aspects of the surgery that went well for future reproduction (e.g., clamping of a blood vessel in the area of interest led to improved surgical outcomes as overall blood loss was reduced).

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the instant disclosure.

DESCRIPTION OF THE FIGURES

Embodiments will be described, by way of example only, with reference to the attached figures, wherein in the figures.

It is understood that throughout the description and figures, like features are identified by like reference numerals.

DETAILED DESCRIPTION

Figure 1A:
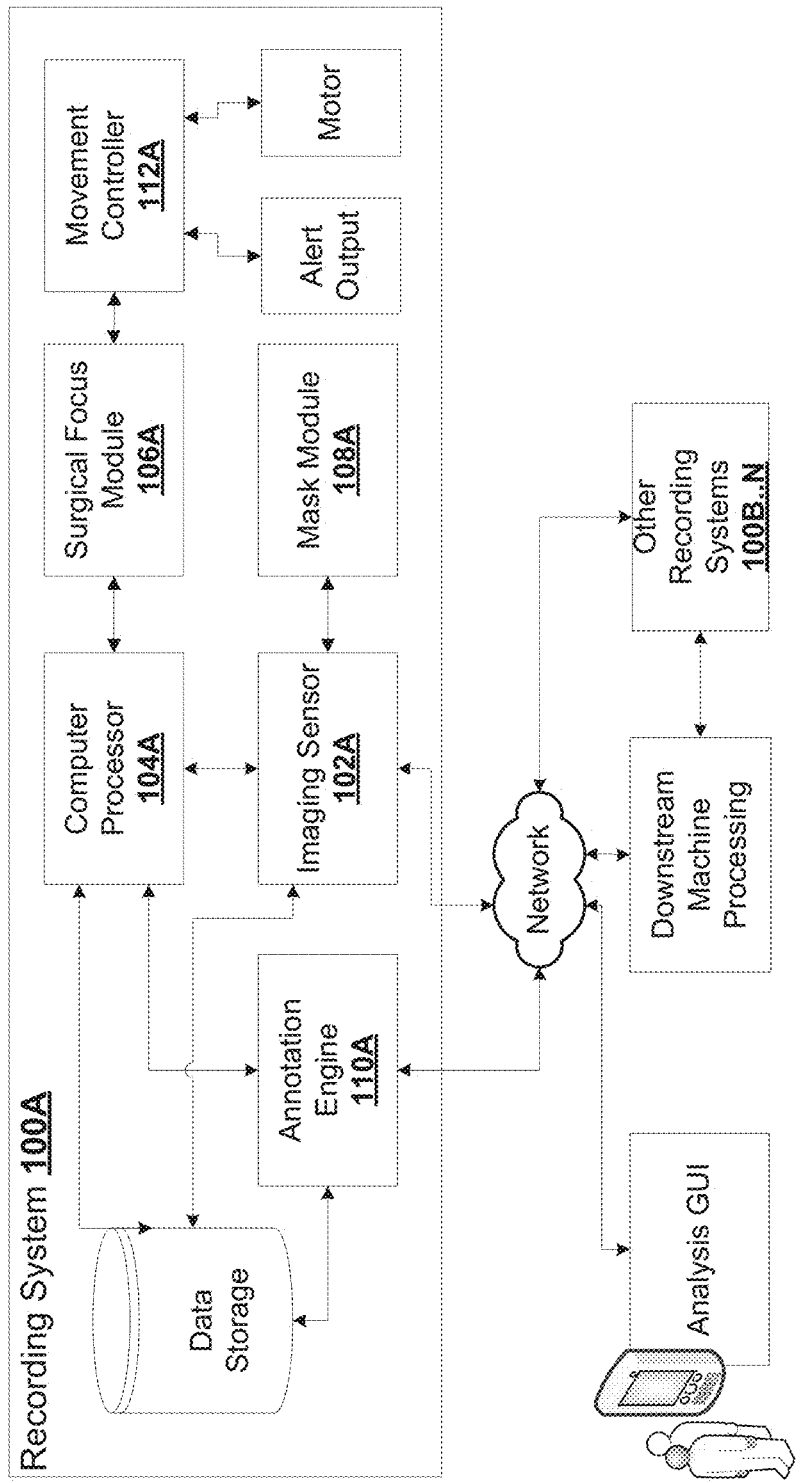
FIG. 1A is an example block schematic of a recording system, according to some embodiments.

As described here, various approaches for an image recording system as described. The system is useful, for example, for surgical procedure recording for purposes beyond simply recording the surgical procedure. The recordings can be processed, for example, by downstream machine learning processes to automatically conduct classifications and/or predictions, which can then be used for enhanced analysis, such as automatically generated annotations for review by a specialist reviewer (e.g., on a graphical user interface), or in some embodiments where there is no specialist reviewer available, machine based procedure "scoring" or identification of critical moments.

This is particularly important where the recordings are used for ensuring patient quality and identifying lessons learned in surgical procedures. Surgical procedures are, by their very nature, often risky, and there are many variables and complicating factors that can either contribute to the success of an operation, or the failure of an operation. Furthermore, there are issues that could arise that could lead to post-operative issues.

In 2000, the Institute of Medicine (US) Committee on Quality of Health Care in America released an eye-opening publication on medical errors, detailing that as many as 98,000 people die from medical errors in hospitals in any given year—a number higher than those who die from motor vehicle accidents, breast cancer, or AIDS. This introduced the idea of systemic redesign to improve patient safety and was reinforced the following year in 2001, when then president of the Institute for Healthcare Improvement published an article titled: "Not again! Preventing errors lies in redesign—not exhortation".

In 2004, Dr. Baker's group in Toronto released "The Canadian Adverse Events Study: the incidence of adverse events among hospital patients in Canada". This paper calculated the overall incidence rate of adverse events at 7.5% in a sample of Canadian hospitals—and identified how a large number of these adverse events were preventable. This paper was seminal in informing the public that the population in Canada is also at high risk for medical adverse events.

Applicants are thus interested in providing improved computational tools to assist healthcare practitioners in being able to reproduce accurately and efficiently aspects of surgical procedure.

High quality intraoperative video capture facilitates better healthcare in many ways, including better surgical training, continued professional development, and error analysis and quality improvement. In open surgery in particular, there is a severe deficiency in the ability to reliably and routinely capture high quality intraoperative video. There exists technology currently being widely adopted in other industries that may help solve this problem.

Applicants have developed a prototype device specifically designed to address the issues that have been identified in previous attempts to record video of open surgery. Variants are described to further refine this prototype, assess it by comparison to the most commonly cited method of currently filming open surgery, and then assesses surgeon's perceptions of the device as well as the video product it produces after deployment in real surgical cases.

Intraoperative video recording can provide trainees with surgical content that they can review in lieu of, or as extra material when they are not in the operating room, and this may help improve their surgical reasoning and technical operative performance. Intraoperative video recording also allows for a larger audience to appreciate the finer details of an operation, perhaps with additional explanation as required.

This is typically referred to as 'telementoring' and is becoming increasingly important in an era of crowded operating rooms with limited time for explanations/live-training. Intraoperative video also facilitates surgical coaching. There have been several different surgical coaching models published and validated in surgical training. These often involve recording surgical trainees while they perform certain skills, and then arranging one-to-one feedback sessions with surgeons to provide feedback specifically on their performance. This video-based coaching has been shown to enhance the quality of surgical training.

Intraoperative video review has also been shown to positively impact the performance of practicing surgeons. This is often also through a coaching framework, as the learning curve for surgery persists well after training is completed, but targeted activities for surgeons, especially with regards to technical performance, are limited.

These aspects are described in relation to the recording devices in various embodiments herein, which can aid in video review through telemonitoring by human reviewers or downstream machine learning processes.

Up until recently, the majority of published literature has been acquired from laparoscopic surgical cases, because these cases necessitate high-quality video to make the operations possible.

Today, the majority of surgical cases are still open cases and unfortunately, there is a paucity in the application of the above-mentioned quality improvement, training, and performance enhancement techniques for those performing open surgery. This is primarily due to limitations in available technology for capturing high quality video of open surgical cases.

Prior attempts to capture intraoperative video of open surgery may not have been successful. These prior attempts include, among others, handheld camcorders, Google Glass, exoscopes, light handle integrated cameras, among others.

One reason is excessive movement. Previous attempts often use a head-mounted, fixed camera which transmits head movements resulting in excessive video frame instability. Another reason is obstruction by members of the surgical team. Prior configurations embedded a camera in the overhead surgical light handle or mounted overhead elsewhere, but the line of sight of the operative field was often obstructed by the heads and bodies of various members of the surgical team.

Accordingly, intraoperative video enables better surgical training, continued performance enhancement and quality improvement initiatives for open surgery; however, there exists a lack of technology to reliably and routinely capture high-quality video of open surgical procedures. Using the limitations of previous capture systems as innovation targets, Applicants developed a prototype camera system and benchmarked it against existing capture technology using objective and subjective evaluation frameworks.

In a simulated operating room environment, there was less movement of the prototype camera measured by a physical sensor, and algorithmic video analysis demonstrated more stable, sharper, higher contrast images but with more surgical field obstruction. In a real operating room environment, surgeons rated the usability of the prototype more favourably for 'weight' and 'would recommend to a colleague', and rated the video product higher for 'camera stability' but lower for 'unobstructed view of the surgical field'. Various embodiments described herein demonstrates a novel and effective method for intraoperative video capture of a surgical procedure (e.g., open surgery).

As noted above, recording surgical procedures is difficult to accurately accomplish due to practical implementation issues that arise from the innate complexity of the surgical environment during the surgical procedures. Applicants have developed an industry leading operating room "black box" that utilizes, among other inputs, recordings of surgical procedures for automatic (or semi-automatic) collation, review, annotation, or generation of derivative insights.

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing implementation of the various example embodiments described herein.

Embodiments of methods, systems, and apparatus are described through reference to the drawings.

FIG. 1A is an example block schematic of a recording system 100A, according to some embodiments. The recording system, for example, can be a body or object mounted system. The body or object mounted system can include an imaging sensor 102A residing within a housing. The recording system 100A can be utilized in concert with other recording systems 100B . . . N. Imaging sensor 102A can be a camera or other type of imaging device, and can, in some embodiments, include additional light emitters to improve a quality of image.

The imaging sensor 102A can have controllable aspects, such as aperture sizing, an ISO level, exposure levels, brightness corrections, among others.

The recording device is coupled to a computer processor 104A that can be used in conjunction with computer memory and data storage, the computer processor configured to receive the stream of image frames from the imaging sensor 102A and to generate control signals to request the repositioning or movement of the imaging sensor 102A or housing such that a field of view is continuously maintained over the visual region of interest.

The housing can be, for example, an armature for an overhead light that is used (e.g., an operating light) where a lighting effect is produced from lighting elements embedded therein (e.g., LEDs or incandescent lights) that are used by the surgeon to shine light open the operating area of the body (or other aspects).

A camera may be embedded therein. The housing can be coupled or have a motor or alert mechanism residing within. The motor can be used for changing aspects of the imaging sensor 102A (e.g., aperture size changing) or moving the imaging sensor 102A, for example, causing rotation or translation thereof.

In another example, the housing can be coupled to a harness or other type of carrying or conveyance mechanism such that the housing is operatively coupled to the body of a human being (or a medical device in the room, such as an instrument panel). As the housing moves around, in the example where it is harnessed to the individual, it is likely to face various obstructions and encounter signal quality issues—however, these are offset by the potential benefits associated with being focused more often on the operative area (e.g., a shoulder mounted camera) from a desirable perspective.

For example, a body-mounted 3-axis motorized gimbal-stabilized camera system for recording open surgery can be provided having a gimbal motor, which could be a self-stabilizing, wearable camera and mount to be worn by a surgeon and/or other member of a surgical team to capture audio and video of surgical procedures in the operating room. The camera or housing can include a motorized gimbal to which a camera is mounted is controllable remotely to maintain the focus as the computing system of some embodiments utilizes remotely-based or onboard computer vision algorithms to manipulate the motorized gimbal to automatically attend to predefined areas of interest, or new areas of interest could be defined intraoperatively.

As described in various embodiments, a surgical focus module 106A can be provided that can be implemented in the form of a physical surgical focus circuit or integrated circuit which is adapted for tracking of objects in a visual region of interest. As described herein, an approach is described that utilizes machine learning approaches for tracking the visual field and attempting to maintain focus on the correct visual field (e.g., tracking a physical object or a center-point, such as a centroid) relating to a surgical procedure in a field of view.

The machine learning approach is described in variants where a trained machine learning data model architecture maintained by the surgical focus module 106A continually processes the stream of image frames to continuously identify the visual region of interest to tracking a physical object relating to the surgical procedure in the field of view. For example, the physical object and the corresponding visual region of interest could include a centroid or a center point, which can then be used to generate a displacement vector data structure when the centroid of the visual region of interest has been displaced between temporally proximate frames of the stream of image frames. The surgical focus module 106A tracks the displacement vector data structure and maintains it across frames such that corrective commands can be issued to the alert output or a motorized output, according to different embodiments.

The displacement vector data structure tracked by the surgical focus module 106A is representative of a directional shift, and can include, for example, directional-based coordinates indicating an amplitude and/or a direction of the shift. The processor then generates a control signal requesting movement of the imaging sensor or the housing in a direction based at least on the displacement vector data structure. A movement controller 112A transforms the displacement vector data structure into corresponding motor commands, for example, by tracking a positional loss relative to having a centroid located within a particular position in the field of vision, and using the displacement vector data structure to generate motorized commands for movement of the recording system 100A.

Transformations can include the tracking or generation of 2D shifts to 3D movement by way of transformation matrices using Jacobians, among others. The 3D movement, depending on the freedom of movement of the recording system 100A, can include rotations (pitch, yaw, roll) about a fixed point, or, where the recording system 100A is on a rail or other type of translation conveyance mechanism, a shift in 3D space. Motorized aspects can include, for example, stepper motors that are controlled through electrical pulses transmitted, for example, from a pulse width modulator or other type of signal generator.

In some embodiments, a mask module 108A is provided as an additional circuit configured for maintain the trained machine learning data model architecture. The mask module 108A can maintain a suitable convolutional neural network, such as a Mask Region-based Convolutional Neural Network (Mask R-CNN) that is adapted for detection of the object and instance segmentation. Not all embodiments are thus limited and other CNNs are possible for use, although a Mask R-CNN was tested in experimental validation. The mask module 108A can provided on a separate processor, such as a special purpose graphics processor to enhance performance and provide parallel computing. In another embodiment, the processor 104A also provides the mask module 108A.

The mask module 108A using the Mask R-CNN can be adapted to predict, for each pixel of an image frame of the stream of frames, a corresponding segmentation mask selected from a plurality of potential segmentation masks, and wherein the visual region of interest is derived at least from the associated segmentation mask corresponding to each pixel. Segmentation masks are useful, especially where there are obstructions.

For example, the plurality of potential segmentation masks can include a first segmentation mask tracking the physical object relating to the surgical procedure in the field of view and one or more additional segmentation masks tracking one or more corresponding obstructions; and the Mask R-CNN can be adapted to utilize the first segmentation mask and the one or more additional segmentation masks together to identify an overall obstruction amount for a particular frame of the stream of frames. The processor can further annotate using annotation engine 110A the stream of image frames with additional metadata indicative of the overall obstruction amount for each frame of the stream of image frames. The output of annotation engine 110A (which can be an annotation circuit) can include data values encapsulated as metadata that are then utilized to create either an annotation data structure free of video media that can be transmitted separately, or combined together with the underlying recording to generate combined output media files (e.g., annotated AVIs, MPEGs, among others).

In a variant embodiment, the Mask R-CNN is pre-trained on a large scale object detection, segmentation, and captioning data set such that the Mask R-CNN is initialized with weights derived from the pre-training to apply transfer learning where training on previously learned tasks is used to enhance learning of a similar but different task.

Training parameters for the Mask-RCNN training parameters can, for example, include a decreasing stepwise learning rate as training progresses through staged epochs. The visual region of interest can, in some instances, be used to crop the stream of image frames, and wherein the computer processor is further configured to store a cropped stream of image frames onto a data storage. This cropping can provide for an improved focus by a reviewer or a downstream machine learning mechanism (e.g., a bleeding predictor mechanism).

Accordingly, the approaches described can include tracking mechanisms (e.g., tracking algorithms) used by the device to centre the surgical field in a visual region of interest relative to what is being captured by the sensor. As described herein, robust neural network-based object detection and tracking could be implemented, and various approaches are possible, including powerful edge computing at the device-level, or through a cloud-computing based architecture. In some embodiments, an autonomous (or semi-autonomous device) can be proposed that that requires less user-input to maintain an optimal intraoperative viewing perspective.

The objective evaluation used for the purposes of this discussion involves multiple algorithms that are currently each executed individually. For example, once the video file is transferred to the computer, an FFMPEG script is executed to sample still frames from the video file. Those still frames are then processed using Python and Tensorflow for object detection and instance segmentation. Numerical output from the object detection is then evaluated by Matlab to calculate bounding box displacement for the motion metric. Cropped image files are then processed by a separate Matlab script for sharpness and brightness/contrast assessment. The bounding box (or other type of bounding region) is utilized to identify the surgical field region of interest such that a geometric centrepoint of the box/rectangle is identified.

This is repeated across multiple frames (e.g., sequential frames or a next frame) such that there are then two points in a 2D coordinate plane and a magnitude of the displacement vector can be determined (which is the square root of the change in the x coordinate squared+the change in the y coordinate squared). A displacement vector can include, for example, a unit vector indicating a direction of displacement, and a magnitude scalar, and this can be stored as a n-tuple (e.g., one value for each linearly independent dimension and one value for the magnitude scalar).

A separate Python script assesses surgical field obstruction. This workflow could be streamlined to a more integrated process whereby a user would provide a video file as an input, decide on the objective metrics of interest and then receive those metrics in a prespecified format. This would provide a more accessible front-end interface where the integration of the various algorithms and scripts would all take place on the backend.

Because all of the objective metrics rely on the surgical focus module 106A, the precision and accuracy of these metrics could be improved through the use of different neural network models. In a variant, additional annotated training data could be used to try to increase model performance, or additional hyperparameter modification may also be able to increase model performance. Furthermore, training the model on a wider variety of surgical procedures may enable for more generalizable detection beyond just the simple skin procedures tested in this project.

Application-specific brightness, contrast, and sharpness metrics could be developed to better evaluate these parameters in a surgical setting. One approach to doing so would be introducing artificial artifact (either blur, or brightness/contrast change) into the existing training data set. This would have to be done at regular, varied intensities of artifact so as to develop an arbitrarily defined continuous score.

The peak artifact ranges could be determined based on what could realistically be seen in the OR setting. This newly developed dataset could be used to train a classification algorithm that would be able to evaluate surgical images and output a score based on the arbitrarily defined scoring system.

Figure 1B:
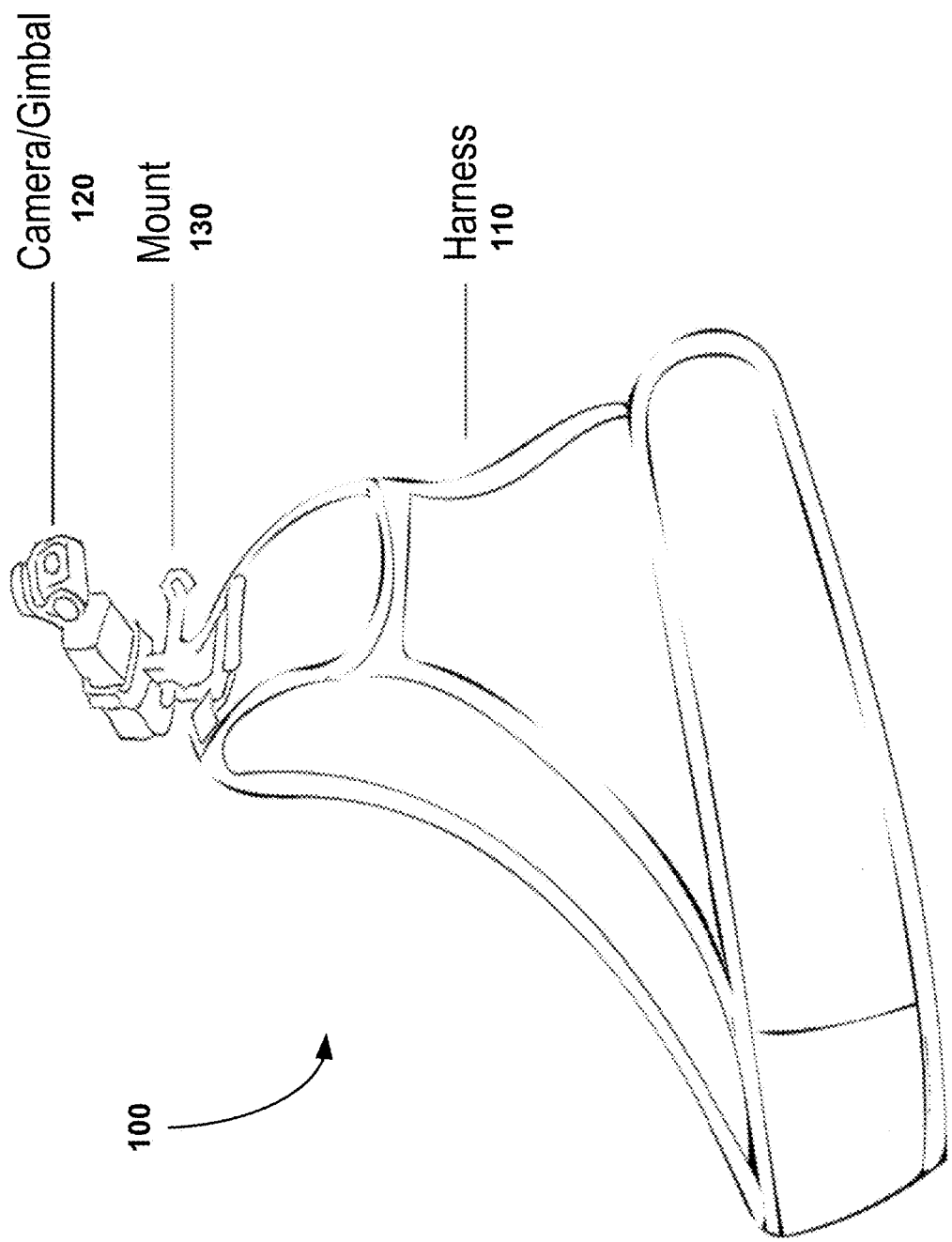
FIG. 1B illustrates an example of a body-mounted camera apparatus, in accordance with some embodiments.

FIG. 1B illustrates an example of a body-mounted camera apparatus 100, in accordance with some embodiments.

The body-mounted camera apparatus 100 comprises a harness 110 configured to be used with a sterile surgical gown, a camera assembly 120 comprising a camera mounted on a gimbal, a control unit 150 coupled to the camera assembly 120, and an apparatus mount 130 coupled at one end to the harness 110 and coupled at the other end to the control unit 150. In some embodiments, the gimbal on which the camera is mounted comprises stabilization module. The control unit 150 may be used to operate the stabilization processing, and communications interfacing, data storage, and power supply (e.g., battery).

In FIG. 1B, the camera is a shoulder mounted camera. The primary hypothesis is that a shoulder-mounted prototype camera system 100 will outperform a head-mounted camera (e.g., head mounted GoPro) when objectively evaluated in a simulated operating room setting. The secondary hypothesis is that surgeons will find this prototype camera system comfortable, easy to use, and minimally intrusive to their regular operative routines.

Applicants assembled and tested a shoulder-mounted, gimbal-stabilized prototype camera. The assembly can include camera/gimbal combination with modified components to produce a shoulder-mounted device that is compatible in the operating room. Initial testing in a simulated operating room setting was conducted to ensure the device is mountable on the surgeon, does not interfere with sterility and can capture high-quality, stable, unobstructed video of the surgical field.

A major challenge of the head-mounted camera are used as the primary outcome measures: excessive movement, obstruction, overexposure, and poor resolution.

During development, as, a strong emphasis for the body worn embodiment was placed on developing a device (e.g., a portable device) that could be worn by the operating surgeon. This was because integrating any new equipment into an existing operating room often requires extensive institutional approval and can be cost and time prohibitive given the specialty personnel and administrative hurdles required to implement these sorts of changes.

Developing a portable, wearable device would also enable research and development in multiple different settings and ultimately lead to a more accessible device.

As surgeons who had personally trialed many of the other cameras and configurations described, Applicants felt that something other than a head-mounted device needed to be developed. This was mainly due to the neck strain experienced by surgeons already wearing too much equipment on their heads as well as the excessive motion artifact transferred to the video footage from a surgeon's head movements while he operates.

Therefore, design objectives were, in some embodiments, to develop a wearable, surgeon-mounted camera that was positioned elsewhere then the head and in such a manner that it would be less susceptible to motion artifact from the surgeon's movements. The secondary design goals consisted of trying to optimize the remainder of the previously described limitations, including resolution, field of view, brightness, and obstruction of the surgical field.

Gimbal stabilization technology is described further in various embodiments, which is an innovative aspect implemented in the prototype camera system.

Figure 2:
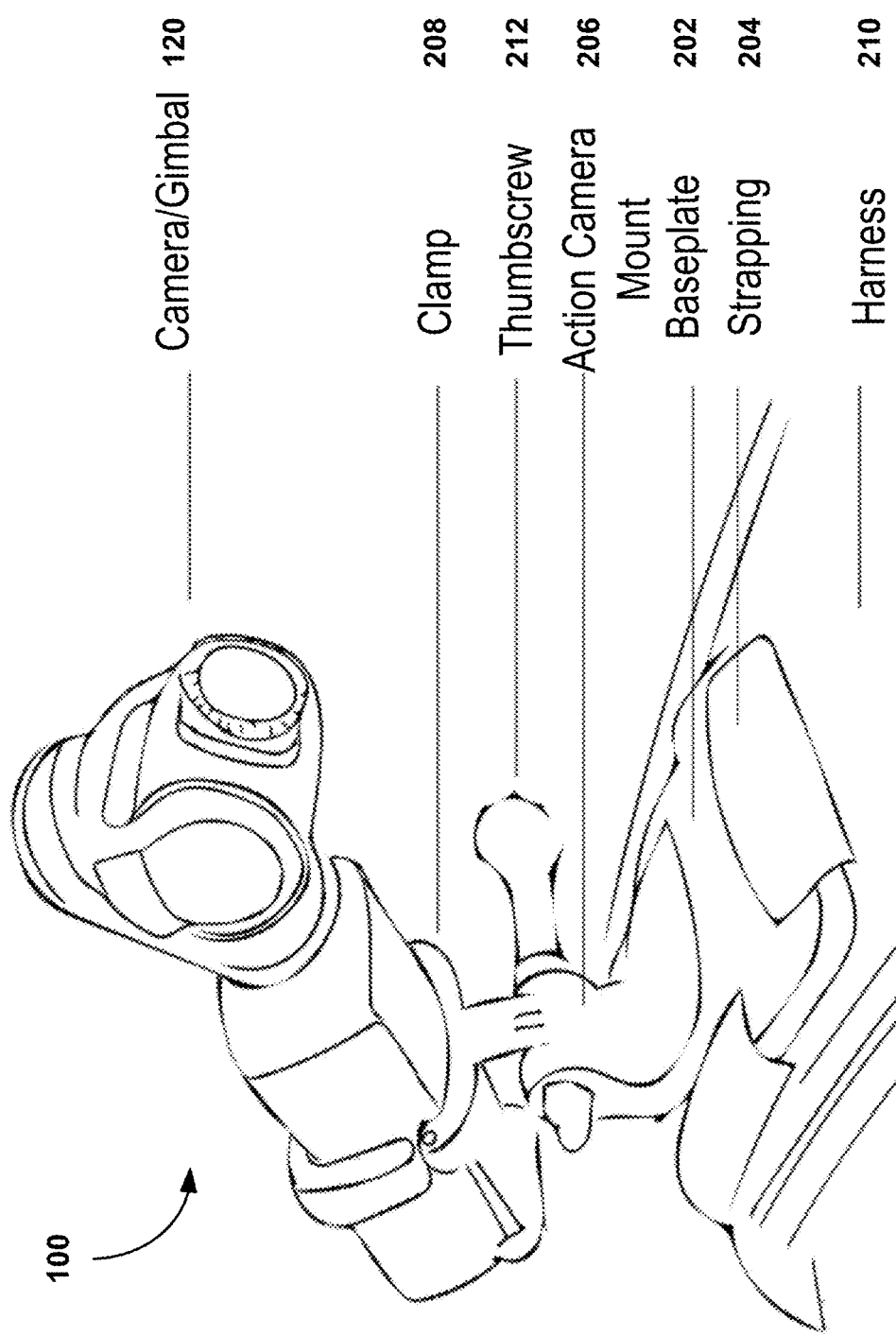
FIG. 2 illustrates an exploded view of another example of a body-mounted camera apparatus in more detail, in accordance with some embodiments.

FIG. 2 illustrates an exploded view of another example of the body-mounted camera apparatus 200 in more detail, in accordance with some embodiments. In some embodiments, the harness 110 comprises a neoprene cross-chest harness 210. In some embodiments, the apparatus mount 130 comprises a base plate 202, strapping 204 to affix the apparatus mount 140 to the harness 110, an action camera mount 206 connected to the base plate 202, and a plastic clamp 208 for receiving a control unit 150 that is coupled to the camera assembly 120. In some embodiments, the body-mounted camera apparatus 200 comprises a thumbscrew 212 for securing the plastic clamp 208 to the base plate 202. In some embodiments, the thumbscrew 212 comprises a M5-0.8 thread screw.

Figure 3:
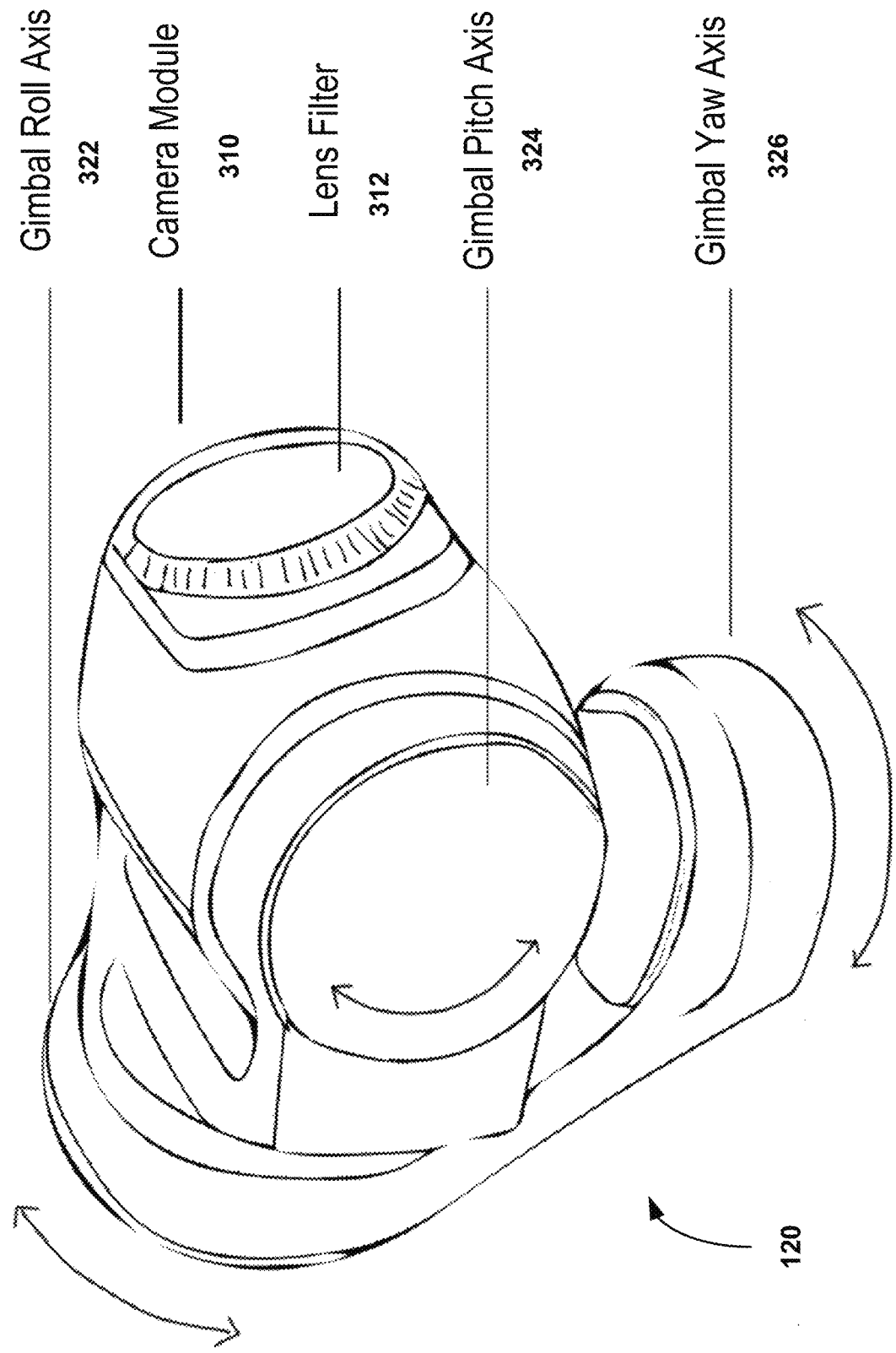
FIG. 3 illustrates an example of a camera assembly, in accordance with some embodiments.

FIG. 3 illustrates an example of a camera assembly 120, in accordance with some embodiments. In some embodiments, the camera assembly 120 comprises a camera module 310 including a lens filter 312, and a gimbal module including a gimbal roll axis 322 for rolling the camera clockwise or counter-clockwise, a gimbal pitch axis 324 for pitching the camera vertically, and a gimbal yaw axis 326 for panning the camera horizontally.

A gimbal, in its most basic form, is a pivoted support that allows the rotation of an object about a single axis. When a set of three gimbals are combined, each mounted on the other with orthogonal pivot axes, this 'three-axis' gimbal structure allows an object mounted on the innermost gimbal to remain independent of the rotation of its support.

When an optical sensor, such as a camera, needs to be pointed from a moving platform to a fixed or moving surface, inertial stabilization platforms have taken advantage of gimbal physics and extended them via servo motion control loops.

Motorized gimbals therefore, are precision electromechanical assemblies designed primarily to isolate the optical system from the disturbance induced by the operating environment, such as various disturbance torques and body motions. A gimbal smooths the angular movements of a camera and provides advantages for acquiring better images. A gimbal can also dampen vibrations, and maintain a camera in a predefined position.

Figure 4:
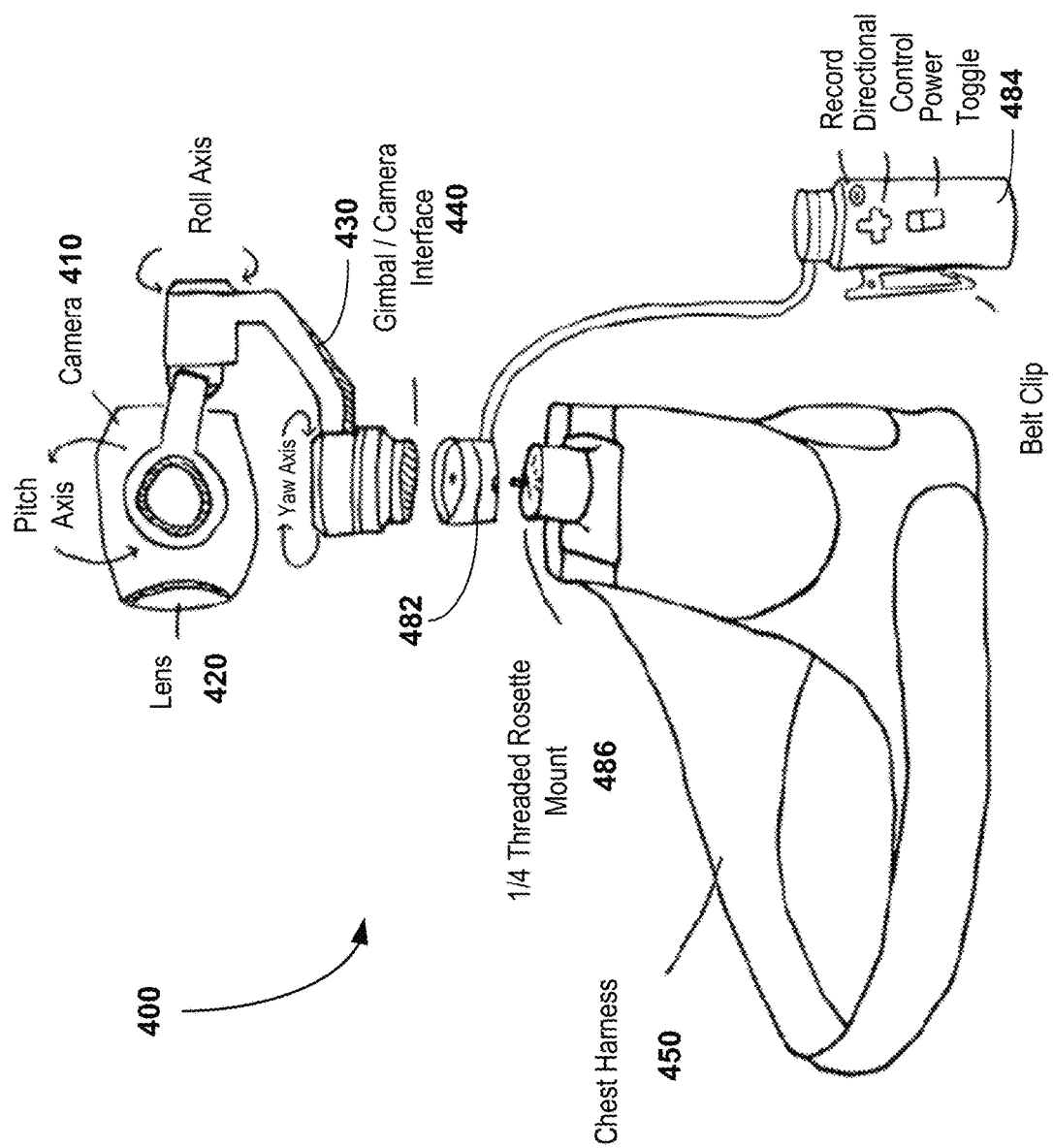
FIG. 4 illustrates another example of a body-mounted camera apparatus, in accordance with some embodiments.

FIG. 4 illustrates another example of a body-mounted camera apparatus 400, in accordance with some embodiments.

The surgeon's shoulder was selected as the mounting site for the gimbal-camera unit of FIG. 4. This was done in an effort to avoid strain on the surgeon's neck caused by the weight of head-mounted accessories and to reduce motion of the camera caused by the surgeon's head movements while operating.

The shoulder position was deemed to be close enough to the surgeon's head such that the line of sight of the camera remained relatively coaxial with the surgeon's line of sight. In order to be used in an operating room setting, the device had to be compatible with a standard surgical gown. A lightweight, breathable, neoprene cross-chest harness was selected to mount the device on the surgeon.

This setup remained compatible with a standard surgical gown as the gimbal-camera unit protruded laterally from the neck of the surgical gown. Because the gimbal-camera unit combined with the grip were together a large unit, the camera-gimbal unit was separated from the grip control unit. An accessory coupling cable was used to maintain device operations. A three-prong action camera style mounting bracket was used to securely mount the gimbal-camera unit on the harness. The 'grip' could then be placed out of the way in the surgeon's pocket.

The body-mounted camera apparatus 400 comprises a camera 410, at least one lens filter 420, a motorized gimbal 430, a gimbal mount 440, a harness 450, a tracking module, and a remote gimbal control. Other elements may be added to the body-mounted camera apparatus 400, such as a gimbal/camera to battery/control unit cable decoupler extender 482, a battery/control unit AC plug adapter 484, and a ¼" screw to mounting adapter 486. In some embodiments, the control unit 150 may be coupled by a tethered connection.

In some embodiments, the camera 120, 410 comprises a lightweight camera capable of recording audio/video. In some embodiments, the focal length of the lens 312, 420 (approximately 26-28 millimetres (mm) @ 35 mm format equivalent) may be selected so that the entire operative field in front of a surgeon would be in view when the surgeon is standing and the camera 120, 410 is mounted on his/her shoulder. The camera 120, 410 may have a manual shutter speed, ISO, and exposure (EV compensation) settings that can be optimized for the operating room setting.

In some embodiments, the at least one lens filter 312, 420 comprises a neutral-density (ND) filter to reduce light intensity of bright overhead operating room lights to allow the camera shutter to function at a rate (the shutter speed) that does not lead to interference with the high frequency flicker of the lights.

In some embodiments, the motorized gimbal 430 comprises a motorized gimbal stabilization device comprising three brushless motors 322, 324, 326 allowing for 3-axis movement of the affixed camera 120, 410. The camera-gimbal combination 120 will use an inertial measurement unit (IMU) coupled to the motorized gimbal 430 for 3-axis stabilization.

In some embodiments, the mount 130, 206, 440 comprises a connection or coupling between the gimbal 430 and the shoulder/body harness 110, 210, 450. This may comprise a plastic, hinged cradle 208 that clamps the gimbal/camera device and interfaces with the harness 110, 210, 450 via, for example, an acrylonitrile butadiene styrene (ABS) plastic adaptor secured with a screw and bolt mechanism.

In some embodiments, the harness 110, 210, 450 comprises a strap or harness which wraps around the body/attaches to the head to which the gimbal mount attaches. In some embodiments, neoprene may be used to ensure lightweight and breathable with Velcro for size universality and secure fixation.

In some embodiments, a tracking module comprises algorithms/software onboard or a remote-based algorithm using computer vision to attend to visual areas of interest by manipulating the motorized gimbal 430 with its affixed camera 120, 410.

In some embodiments, a remote gimbal control comprises a coupled interface allowing remote manipulation of the motorized gimbal 430. In some embodiments, this may be an application (app) on a smartphone or a tablet that connects to the device via Bluetooth, Wifi, or any other wireless protocol connection.

In some embodiments, the means by which the gimbal/camera 120 is mounted to the surgeon's shoulder may be modified to better fit the sterile operating room gown. This may involve an angled support structure so that the actual mount connection is under the gown, but the gimbal/camera 120 sits above the gown with the joint coming through the neck/seam. In some embodiments, the gimbal/camera sits between approximately 5 to 10 centimetres (cm) from the neck and between approximately 3 to 5 cm above the shoulder.

In some embodiments, since the posture of the surgeon and the area of interest is directed downwards, an alternate balancing of the gimbal may be used. Traditionally, the gimbal is balanced such that it faces forward and stabilizes in this position.

In some embodiments, modifications or a different camera entirely may be employed to best suit the OR environment which has extreme highs/lows of lighting exposure and details at varying depths of field making focusing characteristics difficult to manage.

In some embodiments, material or positioning of the body mount 110, 210, 450 may be adjusted.

In some embodiments, the battery/control unit 484 may have a custom mount made that can clip onto the back of the surgeon's scrubs.

Figure 5:
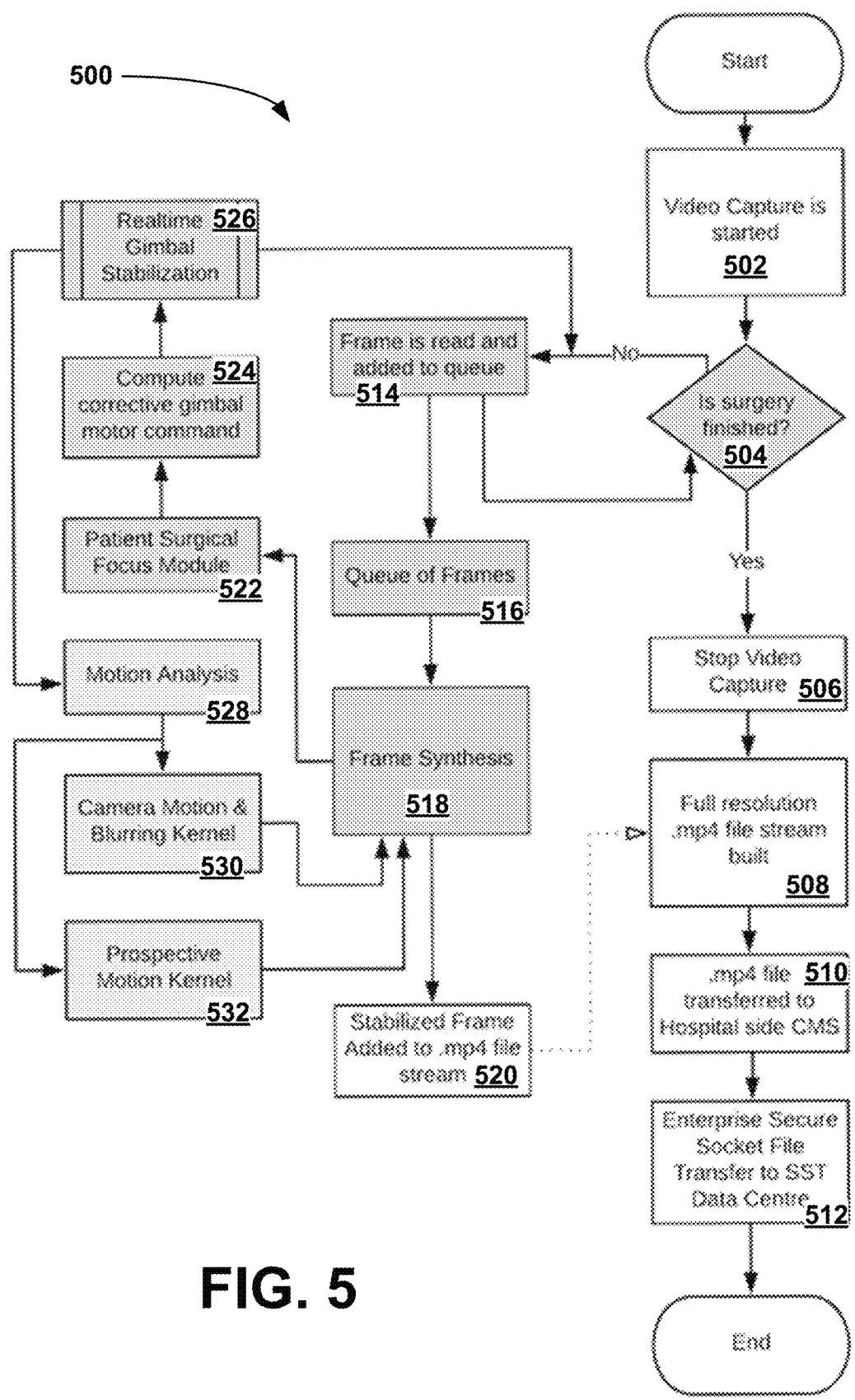
FIG. 5 illustrates, in a workflow diagram, an example of a method of open surgery camera stabilization and object detection, in accordance with some embodiments.

FIG. 5 illustrates, in a workflow diagram, an example of a method 500 of open surgery camera stabilization and object detection, in accordance with some embodiments. The workflow demonstrates physical, gimbal-based stabilization (steps 522 to 526) combined with a digital stabilization algorithm (steps 528 to 532) to create better stabilized images than either approach alone. Steps 504 and 514 to 518 outline decomposition of video to individual frames for analysis and processing and then reassembly to video files. Steps 502, 506 to 512 and 520 outline high level interface with a surgical black box recording device (see FIG. 7 below).

At step 522, the Patient Surgical Focus Module refers to an object detection algorithm that detects the surgical field. The area of interest would be represented as a series of coordinates (X, Y).

At step 524, the compute corrective gimbal motor command provides that if the area of interest is not centred, the change in position (amount of physical motor activation of the gimbal) may be calculated to bring the area of interest into the centre position.

At step 526, the realtime gimbal stabilization comprises a built-in function of the gimbal-camera device. It uses an IMU (inertial motion unit) to detect changes in 3D space/positioning and directly translates that to gimbal motor commands for instant stabilization.

Step 526 feeds down into steps 514 to 518 pertaining to the decomposition of video to individual frames for analysis, processing, and reassembly to video files. This is due to this mechanism used and affecting every subsequent frame. Step 526 feeds down into the digital stabilization algorithm (steps 528 to 532) because the trajectory of movement is sensed by the IMU within the gimbal and can be used to predict future movement within the 'motion analysis' component.

At step 530, the Camera motion and blurring kernel, Gaussian blur may be applied, based on how much the camera is moving, to make this appear smooth.

At step 532, the Prospective Motion Kernel, a 'virtual camera' of future motion adjustments may be predicted, based on the trajectory of the camera.

At step 528, the surgical focus module, may comprise an algorithm designed to detect the surgical field.

In some embodiments, self-stabilization may be the result of an array of electronics, sensors, motors, and physics to cancel out motion instantaneously before it reaches the camera.

Brushless motors (low speed (never full rotation, rapid response, i.e., fine control) may be placed on the three different axes around the camera. IMU (inertial measurement unit=accelerometer+gyroscope+magnetometer) can detect movement in all planes/axes.

A controller may comprise a microchip that receives IMU data and converts to corrective motor commands. When IMU detects movement, this may be sent to the controller which translates to a corrective motor maneuver, instantly or near-instantly.

In some embodiments, a remote-gimbal control may be independent of self-stabilization. Remote-gimbal control may provide commands to the motors of the gimbal to influence the camera. In some embodiments, a tethered device could redirect the camera. In some embodiments, an internal or tethered device could use an algorithm to assist/direct camera movements.

In some embodiments, the tracking algorithm may comprise vision-based tracking and/or object-based tracking.

In vision-based tracking, an object is identified (either click or draw bounding box), software may define ROI based on color/contrast/edges/etc., and as the camera/gimbal move, the software may detect and calculate the change in positioning of the ROI and send a corrective motor command to the gimbal unit.

In object-based tracking, a neural network may be trained to detect objects in the OR (e.g., surgeon's hands, various instruments, members of the operative team, the operative field itself). In some embodiments, a neural network may be sideloaded into onboard controller (therefore can interface with gimbal motors and take advantage of IMU-based stabilization).

In some embodiments, then the camera may be set to stay fixed on a specific trained object and run stabilization at the same time. In some embodiments, occluded image data may be introduced into training sets.

In some embodiments, telemonitoring may be used so that people may view live via a secondary display or a virtual reality headset, and secondary display or headset movements could be sent as motor commands to the gimbal.

In some embodiments, multiple gimbal-mounted cameras may be stitched and they work together to optimize a complete 360 degree recreation of the surgical field.

In some embodiments, a system where an algorithm is trained to detect surgical field, or surgeon's hands, or a particular instrument/marker may be used. For example, a neuronet could be running simultaneously and this detects the objects and provides camera tracking instead of a feature-based as described above.

Figure 6:
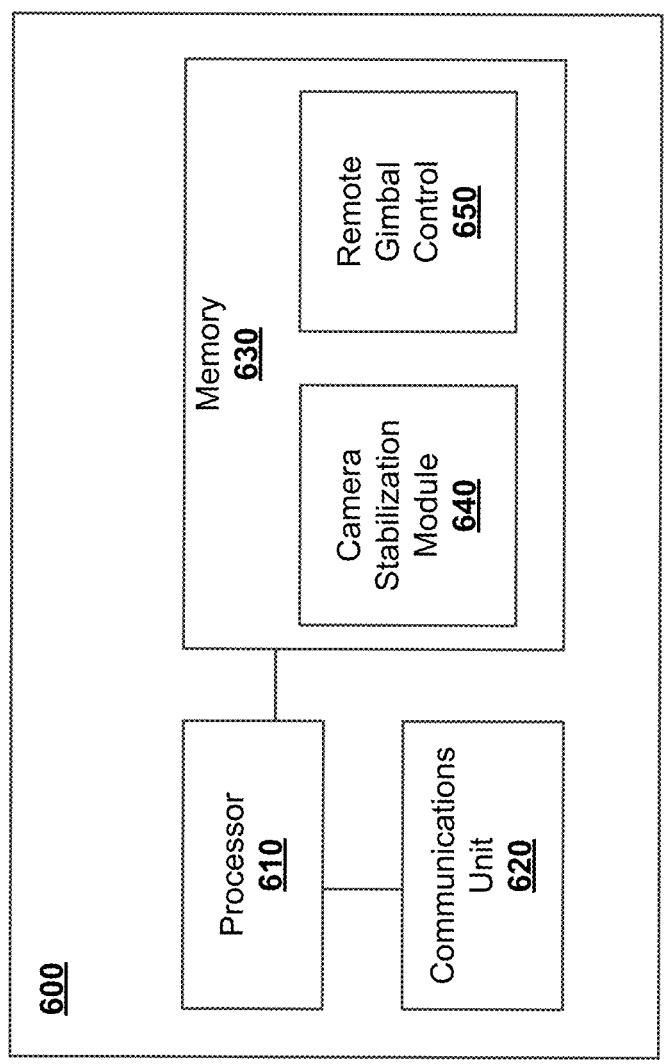
FIG. 6 illustrates, in a component diagram, an example of an open surgery camera controller, in accordance with some embodiments.

FIG. 6 illustrates, in a component diagram, an example of an open surgery camera controller 600, in accordance with some embodiments. The controller 600 comprises a processor 610, communication means 620 for communicating with the camera 120, 410, gimbal or a server, and a memory 630 comprising instructions performed by the processor. The memory 630 may comprise a camera stabilization module 640 storing instructions for camera stabilization (including operations and communications of the control unit 150), and a remote gimbal control module 650 for storing instructions to remotely control the gimbal. Other components may be added to the controller 600, such as a removable storage component (e.g., a MicroSD card) for local storage of data such as full resolution video files. It is understood that storage of camera data may also be stored on a server via communication means 620.

In some embodiments, robotic, computer-vision-based mounts could be placed elsewhere in the operating room to control cameras. These could, for example, be mounted on the boom of an operating room light just above the surgical field. The mount could be fully-articulating with integrated edge-computing ability to run computer vision algorithms. These would be able to detect the surgical field and self-adjust when the optimal view is lost.

In some embodiments, the gimbal-stabilized mount could be placed on the surgeon's head, if the camera/gimbal combination became small enough and lightweight enough to do so in a safe and comfortable manner.

In some embodiments artificial intelligence (AI)/machine learning (ML) could be applied where the device learns a particular surgeons movements/positioning for a specific case, and then this can be used to produce better, smoother footage and attend to the specific areas of interest for that case. For example, if a surgeon always tilts to one side when performing a specific operative maneuver, the stabilizer mount could anticipate this and adjust accordingly.

In some embodiments, advanced digital stabilization technologies may augment physical stabilizers.

In some embodiments, advanced stabilization could be incorporated into other wearable cameras, like smart glasses.

In some embodiments, integration of 'fused video stabilization' that integrates optical image stabilization and electronic image stabilization (EIS) may be provided. EIS may incorporate AI-driven algorithms for additional stability.

In some embodiments, the body-mounted camera may be used for routine intraoperative video recording. The device may be affixed to one or more members of the surgical team and turned on at the beginning of the case. It captures audio/video and stores on a removable medium and/or streams through a wired or wireless connection to a local server (e.g., black box platform; see below). It may record for the entire case. The motorized-gimbal may serve to stabilize the camera throughout the case. With the addition of computer vision, the area of interest would be defined to the camera at the beginning of the case and the camera would attend to this specific region and incorporate stabilization maneuvers throughout the case by manipulation of the gimbal motors to maintain a smooth video and to keep the operative area of interest in field.

In some embodiments, the body-mounted camera may be used for tele-monitoring of surgical cases. The device may function as above, but the audio/video (A/V) feed would be available via network stream to coupled devices, such as smartphone/tablet/computer, and the device could be manipulated remotely via these devices to give an enhanced/interactive viewing experience. This could be used by surgical trainees, for example, to follow along for educational purposes during a case.

In some embodiments, the body-mounted camera may be used for Integration with a surgical black box (see below). The device would function as above, and the A/V data could be used in real-time (or near-real-time) or later for analysis by the surgical black box.

In some embodiments, the technology described above could serve to overcome barriers to recording open surgery. Where intraoperative video recording is routine (because of integrated cameras necessary for the procedures—such as laparoscopic and robotic surgery), that video has educational benefits in training new surgeons, benefits in continuing education and performance enhancement of practicing surgeons, and allows for error analysis and quality improvement initiatives. For example, the technology described above could allow for a surgical blackbox to be translated to open-type surgery and confer all the benefits it has already demonstrated in laparoscopic surgery.

Figure 7:
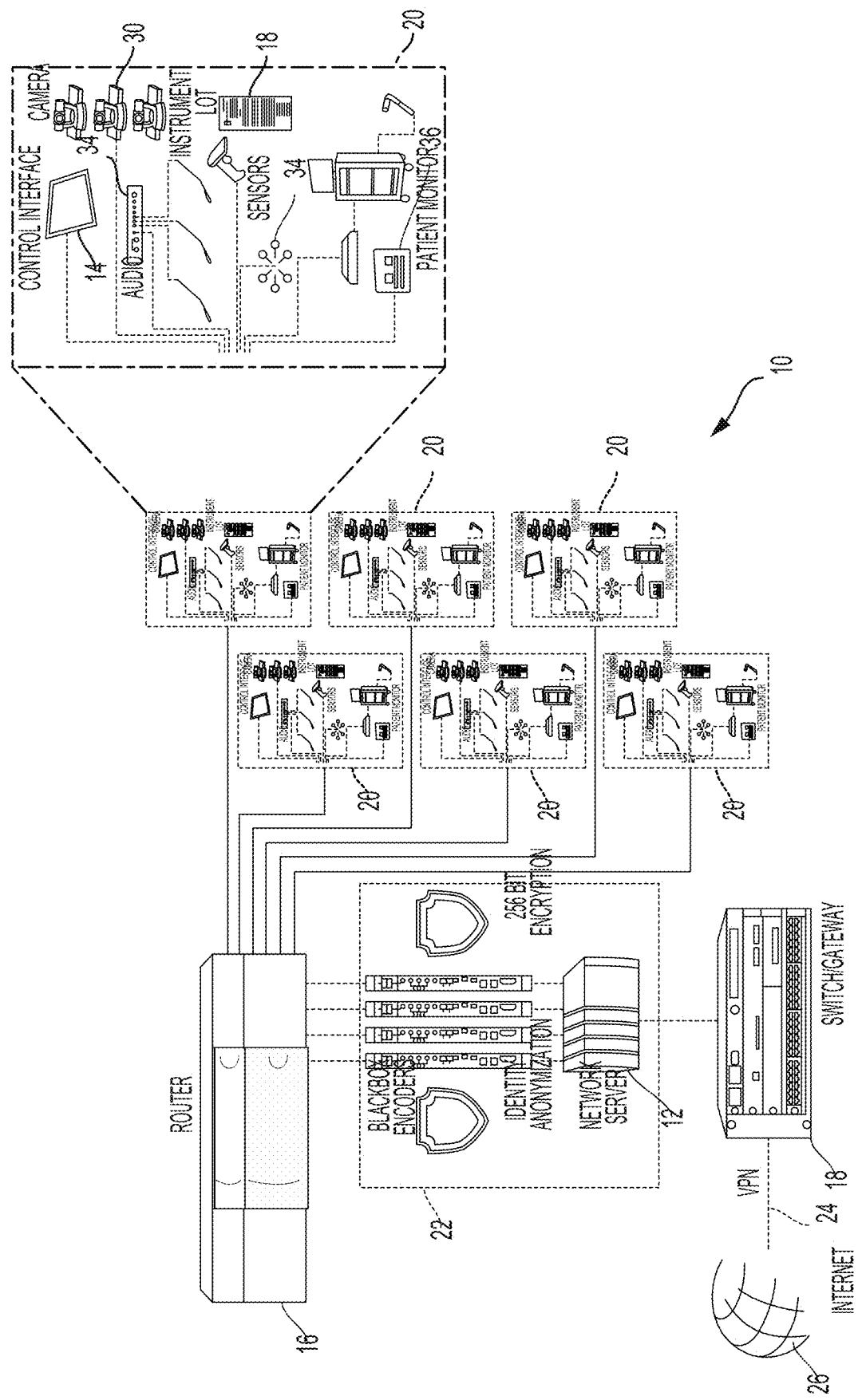
FIG. 7 illustrates a schematic of an architectural platform for data collection in a live OR setting or patient intervention area, in accordance with some embodiments.

FIG. 7 illustrates a schematic of an architectural platform 10 for data collection in a live OR setting or patient intervention area, in accordance with some embodiments. Further details regarding data collection and analysis are provided in International (PCT) Patent Application No. PCT/CA2016/000081 entitled "OPERATING ROOM BLACK-BOX DEVICE, SYSTEM, METHOD AND COMPUTER READABLE MEDIUM FOR EVENT AND ERROR PREDICTION" and filed Mar. 26, 2016 and International (PCT) Patent Application No. PCT/CA2015/000504, entitled "OPERATING ROOM BLACK-BOX DEVICE, SYSTEM, METHOD AND COMPUTER READABLE MEDIUM" and filed Sep. 23, 2015, the entire contents of each of which is hereby incorporated by reference.

The data collected relating to the handwashing activity can be correlated and/or synchronized with other data collected from the live OR setting by the platform 10. For example, hand washing activity for a particular individual participating in a surgery can be linked and/or synchronized with other data collected from the live OR setting for the surgery. This can also include data post-surgery, such as data related to the outcome of the surgery.

The platform 10 can collect raw video data for processing in order to detect surgical tool usage and/or technical performance, and performance measurement. The output data (surgical tool usage and/or technical performance tracking and performance measurement) can be aggregated with other data collected from the live OR setting for the surgery or otherwise generated by platform 10 for analytics. In some embodiments, the output data is collected in real-time or near-real-time. In some embodiments, the camera recordings and other sensor data are processed and analysed in real-time or near-real-time for assessment of at least one of technical performance, device performance, errors or events for real-time or near-real-time feedback to the live OR setting.

The platform 10 can collect raw video data for processing in order to track and measure surgical tools and/or technical performance as described herein. The output data (e.g., performance measurement and/or alerts) can be aggregated with other data collected from the live OR setting for surgery or otherwise generated by platform 10 for analytics. In some embodiments, the output data is collected in real-time or near-real-time. In some embodiments, the camera recordings and other sensor data are processed and analysed in real-time or near-real-time for assessment of at least one of technical performance, device performance, errors or events for real-time or near-real-time feedback to the live OR setting.

The platform 10 includes various hardware components such as a network communication server 12 (also "network server") and a network control interface 14 (including monitor, keyboard, touch interface, tablet, processor and storage device, web browser) for on-site private network administration.

Multiple processors may be configured with operating system and client software (e.g., Linux, Unix, Windows Server, or equivalent), scheduling software, backup software. Data storage devices may be connected on a storage area network.

The platform 10 can include a surgical or medical data encoder 22. The encoder may be referred to herein as a data recorder, a "black-box" recorder, a "black-box" encoder, and so on. The platform 10 may also have physical and logical security to prevent unintended or unapproved access. A network and signal router 16 connects components.

The platform 10 includes hardware units 20 that include a collection or group of data capture devices for capturing and generating medical or surgical data feeds for provision to encoder 22. The hardware units 20 may include cameras 30 (e.g., including cameras for capturing video for surgical tool tracking and/or technical performance, and performance measurement) internal to patient to capture video data for provision to encoder 22. The encoder 22 can implement the surgical tool and/or technical performance tracking, and performance measurement described herein in some embodiments. The video feed may be referred to as medical or surgical data. An example camera 30 is a laparoscopic or procedural view camera resident in the surgical unit, ICU, emergency unit or clinical intervention units. Example video hardware includes a distribution amplifier for signal splitting of Laparoscopic cameras. The hardware units 20 can have audio devices 32 mounted within the surgical unit, ICU, emergency unit or clinical intervention units to provide audio feeds as another example of medical or surgical data. Example sensors 34 installed or utilized in a surgical unit, ICU, emergency unit or clinical intervention units include but not limited to: environmental sensors (e.g., temperature, moisture, humidity, etc., acoustic sensors (e.g., ambient noise, decibel), electrical sensors (e.g., hall, magnetic, current, mems, capacitive, resistance), flow sensors (e.g., air, fluid, gas) angle/positional/displacement sensors (e.g., gyroscopes, altitude indicator, piezoelectric, photoelectric), and other sensor types (e.g., strain, level sensors, load cells, motion, pressure). The sensors 34 provide sensor data as another example of medical or surgical data. The hardware units 20 also include patient monitoring devices 36 and an instrument lot 18.

The customizable control interface 14 and GUI (may include tablet devices, PDA's, hybrid devices, convertibles, etc.) may be used to control configuration for hardware components of unit 20. The platform 10 has middleware and hardware for device-to-device translation and connection and synchronization on a private VLAN or other network. The computing device may be configured with anonymization software, data encryption software, lossless video and data compression software, voice distortion software, transcription software. The network hardware may include cables such as Ethernet, RJ45, optical fiber, SDI, HDMI, coaxial, DVI, component audio, component video, and so on to support wired connectivity between components. The network hardware may also have wireless base stations to support wireless connectivity between components.

The platform 10 can include anonymization software for anonymizing and protecting the identity of all medical professionals, patients, distinguishing objects or features in a medical, clinical or emergency unit. This software implements methods and techniques to detect facial, distinguishing objects, or features in a medical, clinical or emergency unit and distort/blur the image of the distinguishing element. The extent of the distortion/blur is limited to a localized area, frame by frame, to the point where identity is protected without limiting the quality of the analytics. The software can be used for anonymizing hand washing activity video data as well.

Data encryption software may execute to encrypt computer data in such a way that it cannot be recovered without access to the key. The content may be encrypted at source as individual streams of data or encrypted as a comprehensive container file for purposes of storage on an electronic medium (i.e., computer, storage system, electronic device) and/or transmission over Internet 26. Encrypt/decrypt keys may either be embedded in the container file and accessible through a master key, or transmitted separately.

Lossless video and data compression software executes with a class of data compression techniques that allows the original data to be perfectly or near perfectly reconstructed from the compressed data.

Device middleware and hardware may be provided for translating, connecting, formatting and synchronizing of independent digital data streams from source devices. The platform 10 may include hardware, software, algorithms and methods for the purpose of establishing a secure and reliable connection and communication directly, or indirectly (via router, wireless base station), with the OR encoder 22, and third-party devices (open or proprietary) used in a surgical unit, ICU, emergency or other clinical intervention unit.

The hardware and middleware may assure data conformity, formatting and accurate synchronization. Synchronization may be attained by utilizing networking protocols for clock synchronization between computer systems and electronics devices over packet-switched networks like NTP, etc.

The encoder 22 can implement the surgical tool and/or technical performance tracking and performance measurement described herein in some embodiments. The encoder 22 can provide video data and other data to another server for surgical tool and/or technical performance tracking and performance measurement described herein in some embodiments. The OR or Surgical encoder (e.g., encoder 22) may be a multi-channel encoding device that records, integrates, ingests and/or synchronizes independent streams of audio, video, and digital data (quantitative, semi-quantitative, and qualitative data feeds) into a single digital container. The digital data may be ingested into the encoder as streams of metadata and is sourced from an array of potential sensor types and third-party devices (open or proprietary) that are used in surgical, ICU, emergency or other clinical intervention units. These sensors and devices may be connected through middleware and/or hardware devices which may act to translate, format and/or synchronize live streams of data from respected sources.

The Control Interface (e.g., 14) may include a Central control station (non-limiting examples being one or more computers, tablets, PDA's, hybrids, and/or convertibles, etc.) which may be located in the clinical unit or another customer designated location. The Customizable Control Interface and GUI may contain a customizable graphical user interface (GUI) that provides a simple, user friendly and functional control of the system.

The encoder 22 may be responsible for synchronizing all feeds, encoding them into a signal transport file using lossless audio/video/data compression software. Upon completion of the recording, the container file will be securely encrypted. Encrypt/decrypt keys may either be embedded in the container file and accessible through a master key, or transmitted separately. The encrypted file may either be stored on the encoder 22 or stored on a Storage area network until scheduled transmission.

According to some embodiments, this information then may be synchronized (e.g., by the encoder 22) and/or used to evaluate: technical performance of the healthcare providers; non-technical performance of the clinical team members; patient safety (through number of registered errors and/or adverse events); occupational safety; workflow; visual and/or noise distractions; and/or interaction between medical/surgical devices and/or healthcare professionals, etc. According to some embodiments, this may be achieved by using objective structured assessment tools and questionnaires and/or by retrieving one or more continuous data streams from sensors 34, audio devices 32, an anesthesia device, medical/surgical devices, implants, hospital patient administrative systems (electronic patient records), or other data capture devices of hardware unit 20. According to some embodiments, significant "events" may be detected, tagged, time-stamped and/or recorded as a time-point on a timeline that represents the entire duration of the procedure and/or clinical encounter. The timeline may overlay captured and processed data to tag the data with the time-points. In some embodiments, the events may be surgical tool and/or technical performance tracking events or episodes.

Upon completion of data processing and analysis, one or more such events (and potentially all events) may be viewed on a single timeline represented in a GUI, for example, to allow an assessor to: (i) identify event clusters; (ii) analyze correlations between two or more registered parameters (and potentially between all of the registered parameters); (iii) identify underlying factors and/or patterns of events that lead up to adverse outcome; (iv) develop predictive models for one or more key steps of an intervention (which may be referred to herein as "hazard zones") that may be statistically correlated to error/adverse event/adverse outcomes, v) identify a relationship between performance outcomes and clinical costs. These are non-limiting examples of uses an assessor may make of a timeline presented by the GUI representing recorded events.

Analyzing these underlying factors according to some embodiments may allow one or more of: (i) proactive monitoring of clinical performance; and/or (ii) monitoring of performance of healthcare technology/devices (iii) creation of educational interventions—e.g., individualized structured feedback (or coaching), simulation-based crisis scenarios, virtual-reality training programs, curricula for certification/re-certification of healthcare practitioners and institutions; and/or identify safety/performance deficiencies of medical/surgical devices and develop recommendations for improvement and/or design of "intelligent" devices and implants—to curb the rate of risk factors in future procedures and/or ultimately to improve patient safety outcomes and clinical costs.

The device, system, method and computer readable medium according to some embodiments, may combine capture and synchronization, and secure transport of video/audio/metadata with rigorous data analysis to achieve/demonstrate certain values. The device, system, method and computer readable medium according to some embodiments may combine multiple inputs, enabling recreation of a full picture of what takes place in a clinical area, in a synchronized manner, enabling analysis and/or correlation of these factors (between factors and with external outcome parameters (clinical and economical). The system may bring together analysis tools and/or processes and using this approach for one or more purposes, examples of which are provided herein.

Beyond development of a data platform 10, some embodiments may also include comprehensive data collection and/or analysis techniques that evaluate multiple aspects of any procedure including video data internal to the patient for surgical tool usage and/or technical performance tracking, and performance measurement. One or more aspects of embodiments may include recording and analysis of video, audio and metadata feeds in a synchronized fashion. The data platform 10 may be a modular system and not limited in terms of data feeds—any measurable parameter in the OR/patient intervention areas (e.g., data captured by various environmental acoustic, electrical, flow, angle/positional/displacement and other sensors, wearable technology video/data stream, etc.) may be added to the data platform 10. One or more aspects of embodiments may include analyzing data using validated rating tools which may look at different aspects of a clinical intervention.

According to some embodiments, all video feeds and audio feeds may be recorded and synchronized for an entire medical procedure. Without video, audio and data feeds being synchronized, rating tools designed to measure the technical skill and/or non-technical skill during the medical procedure may not be able to gather useful data on the mechanisms leading to adverse events/outcomes and establish correlation between performance and clinical outcomes.

Figure 8:
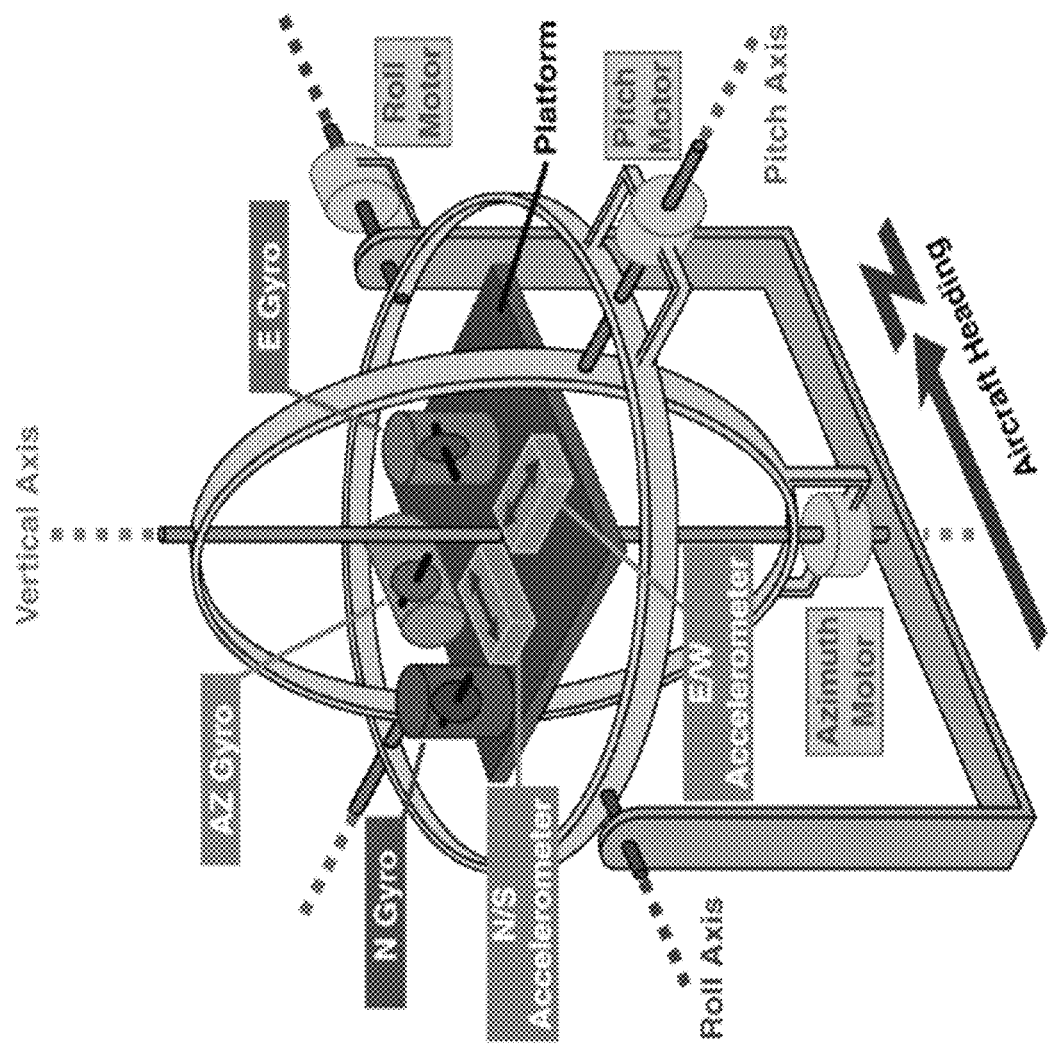
FIG. 8 depicts an example of a motorized gimbal assembly and FIG. 9 outlines an example control loop that would be used for gimbal stabilization of its camera payload.
Figure 9:
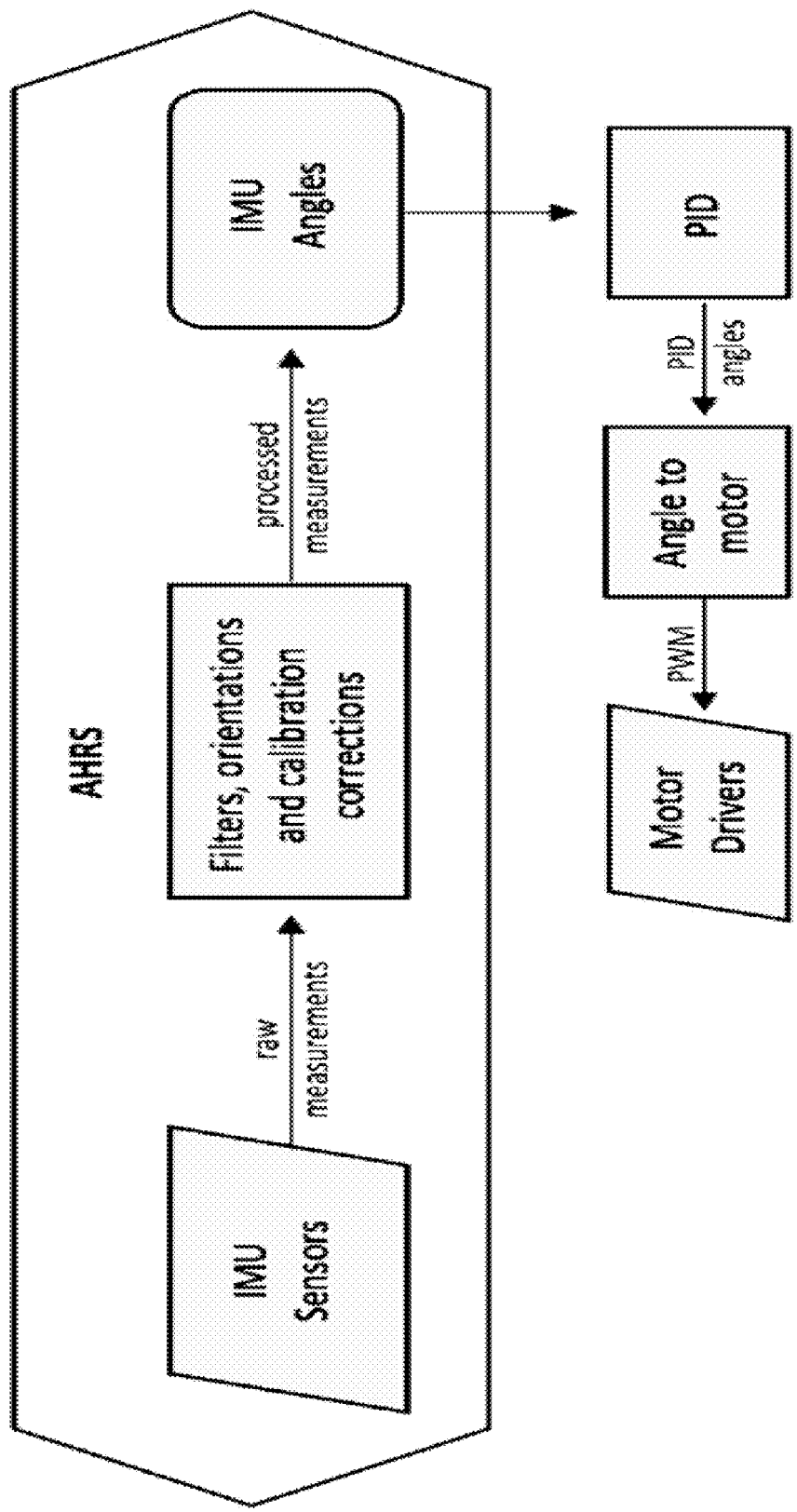

FIG. 8 depicts an example of a motorized gimbal assembly and FIG. 9 outlines an example control loop that would be used for gimbal stabilization of its camera payload.

Figure 10:
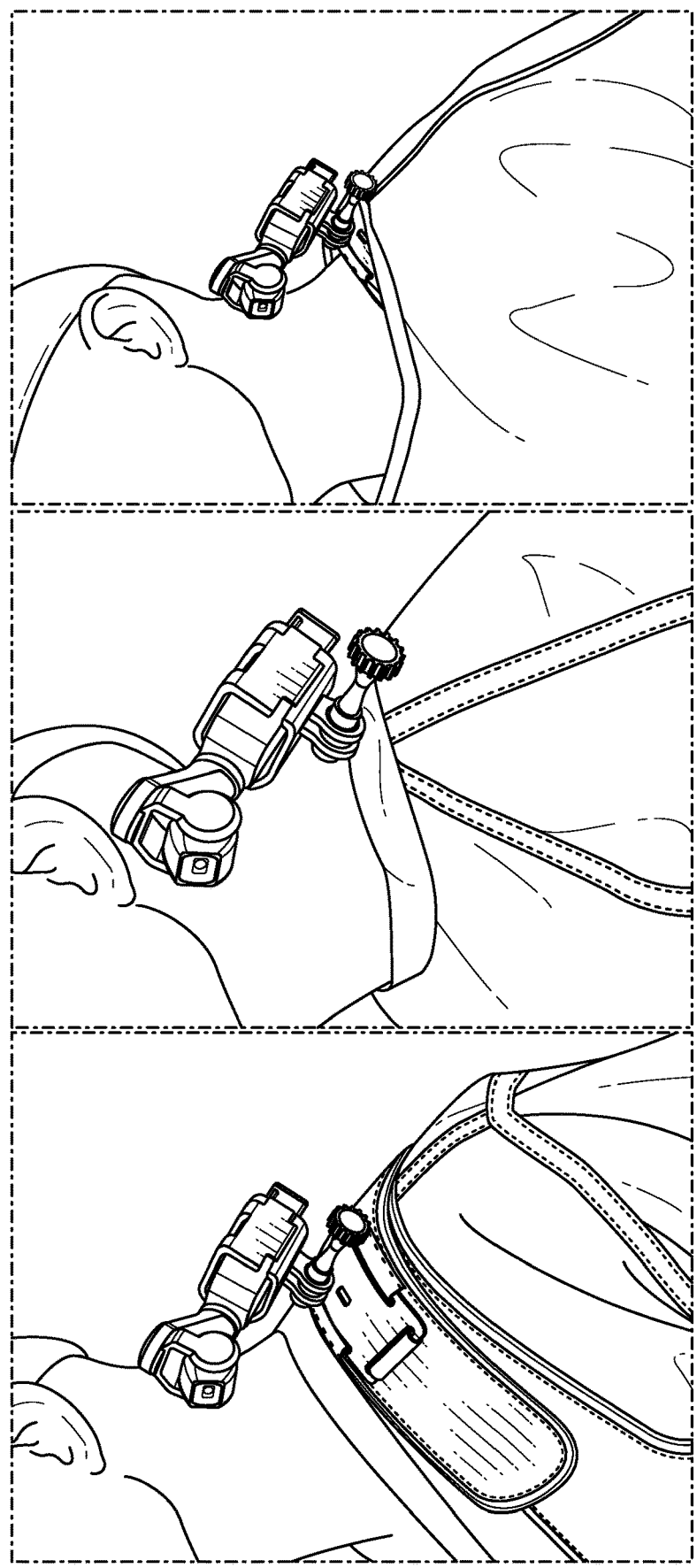
FIG. 10 is a set of photographs provided to illustrate a prototype version mounted on a surgeon's shoulder, according to some embodiments.

FIG. 10 is a set of photographs provided to illustrate a prototype version mounted on a surgeon's shoulder, according to some embodiments.

Gimbal stabilization can be utilized to decrease an amount of camera movement during a surgical case.

Inertial Measurement Units (IMUs) are small electronic devices consisting of some combination of gyroscopes, accelerometers and magnetometers, that, when combined, can accurately measure the orientation of a device in 3D space.

The IMU typically consists of a 3-axis accelerometer and 3-axis gyroscope, and may also include a magnetometer. The IMU is typically positioned onto the gimbal's camera mount. The Attitude Heading and Reference System (AHRS) calculates orientation angles based on the corrected IMU measurements. Based on AHRS data, the Proportional Integral Derivate (PID) angles are calculated and sent via Pulse-Width Modulation (PWM) to a motor driver, which is a moving camera, to correct position.

To quantify the amount of movement of the prototype camera system as well as the head-mounted GoPro, an IMU was designed such that it could be affixed to either device and collect device positional data. The sensor used was the Ultimate Sensor Fusion Solution.

This sensor integrates the MPU9250 IMU (InvenSense, TDK Corp.), the M24512 I2C EEPROM (STMicroelectronics N.V.), and the EM7180 sensor hub (EM Microelectronic-Marin SA). The MPU9250 IMU is a nine-axis microelectromechanic system (MEMS) motion sensor with embedded accelerometers, gyroscopes and magnetometers. The 64 Kbyte M24512 I2C EEPROM stores the sensor configuration file and warm start parameters, which allows for faster initialization times by saving previous initialization and calibration parameters. The EM7180 is a sensor fusion hub (or motion sensor co-processor) that takes sensor data from a slave accelerometer, gyroscope, and magnetometer and fuses them.

This additional processor allows for better sensor data provided by the MPU9250, excellent dynamic calibration and filtering algorithms, and higher processing speeds. The sensor was coupled to a Teensy 3.5 microdevelopment board, containing a 120 MHz Cortex-M4F processor and USB and SD card interfaces (PJRC.COM, LLC).

Quaternions are the preferred mathematical number system for calculations involving three-dimensional rotations, however Euler angle representations in the form of yaw, pitch, and roll angles are often reported as they are conceptually more straightforward.

The IMU sensor uses a proprietary, integrated adaptive algorithm to determine quaternions.

These quaternions are then used to construct a 3×3 rotation matrix and the yaw, pitch, and roll Euler angles can then be constructed from the direction cosine elements of the matrix (Equation 0-1, Equation 0-2).

$$a12 = 2.0f*(q[1]*q[2]+q[0]*q[3]);$$

$$a22 = a[0]*q[0]+q[1]*q[1]-q[2]*q[2]-q[3]*q[3];$$

$$a31 = 2.0f*(q[0]*q[1]+q[2]*q[3]);$$

$$a32 = 2.0f*(q[1]*q[3]-q[0]*q[2]);$$

$$a33 = q[0]*q[0]-q[1]*q[1]-q[2]*q[2]+q[3]*q[3];$$

Equation 0-1: Constructing the Rotation Matrix from Quaternion Values

Elements of the 3×3 Rotation Matrix are Calculated from Quaternion Values $$pitch = -a\sin(a32);$$

$$roll = a\tan(a31, a33);$$

$$yaw = a\tan(a12, a22);$$

Equation 0-2: Calculating Euler Angles.

Euler Angle are Calculated from the Direction Cosine Elements of the Rotation Matrix The Arduino Integrated Development Environment (IDE) was used for sensor programming and interfacing. The sample code provided with the sensor was modified for use in this project. Key elements of the code include sensor initialization and autocalibration, including continuous hard and soft-iron magnetic auto-calibration, quaternion output and calculation and output of associated Euler angles, and SD card data logging. For the purposes of this project, data was sampled at 10 Hz.

Before using the IMU sensor to compare movement of the two camera systems, concurrent validity was established using a geared tripod head (Manfrotto MHX-PRO, Lino Manfrotto+Co. Spa). Concurrent validity is demonstrated when a test correlates well with a measure that has previously been validated.

Figure 11:
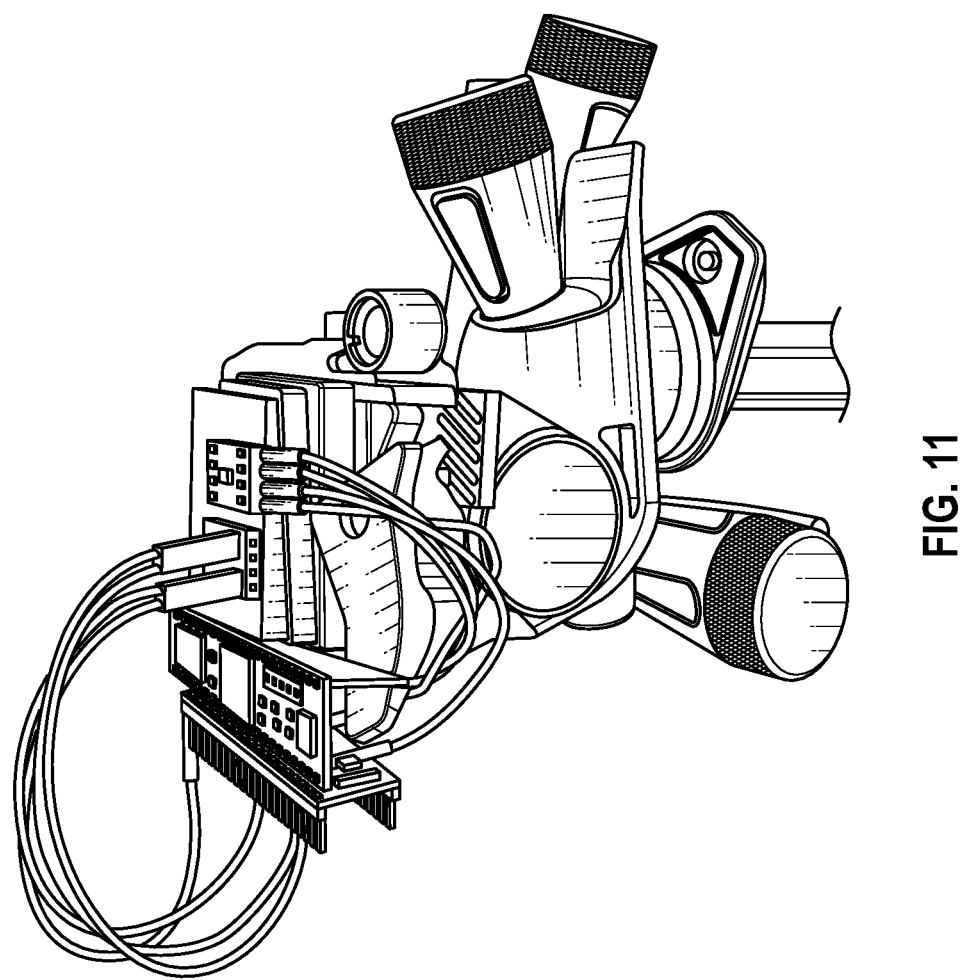
FIG. 11 is a photograph of an IMU.

In this case, the test was the positional orientation reported by the IMU sensor and the measure was the position of the geared tripod head. A geared tripod head is a tripod head that allows for measured adjustment in 3 perpendicular axes. Each individual axis is controlled by a knob and the position can be tuned precisely using a protractor-like scale. Two IMU sensors that were to be used for comparing camera movement were rigidly attached to the center of the geared tripod head for simultaneous validation testing (FIG. 11).

The measurable range of the geared tripod head was −20 to 90 degrees for the pitch and roll axes and −180 to 180 degrees for the yaw axis. Each 5-degree marking was considered a 'stop' for validation testing. This amounted to a total of 23 stops each for the pitch and roll axes and 73 stops for the yaw axis. A random number generator was used to determine the order of the validation sequence.

For each testing position, the geared tripod head was adjusted to the specified position. Once positioned, a keypress initiates datalogging on the sensor. Three seconds (30 values at 10 hz) were averaged to represent the final sensor reading which would then be compared to the actual position on the geared tripod head. Between each validation stop, the geared tripod was returned to a zeroed state.

Agreement between the two measurement techniques was assessed using Pearson's correlation coefficient and also by Bland-Altman plot analysis. Pearson's correlation coefficient alone is not adequate for establishing concurrent validity because the technique doesn't account for systemic biases that may be present in measurements and therefore Bland-Altman plots are the preferred method of evaluating agreement between two measurement techniques.

Bland-Altman plots quantify agreement between two quantitative measurements by constructing limits of agreement, which are calculated by using the mean and the standard deviation of the differences between two measurements.

Figure 12:
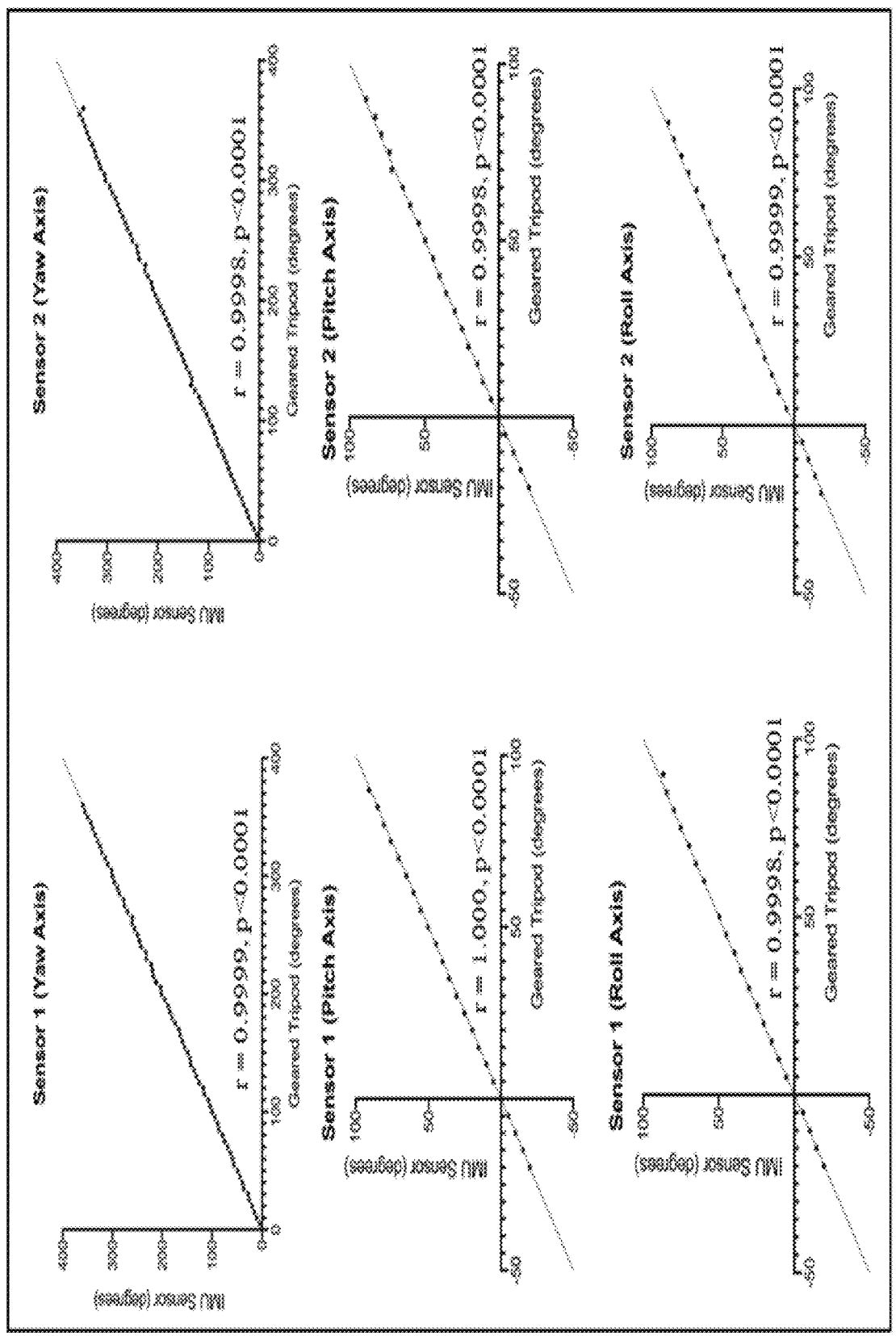
FIG. 12 shows agreement as assessed by the Pearson correlation coefficient and FIG. 13 shows the Bland-Altman plots for the same comparison.
Figure 13:
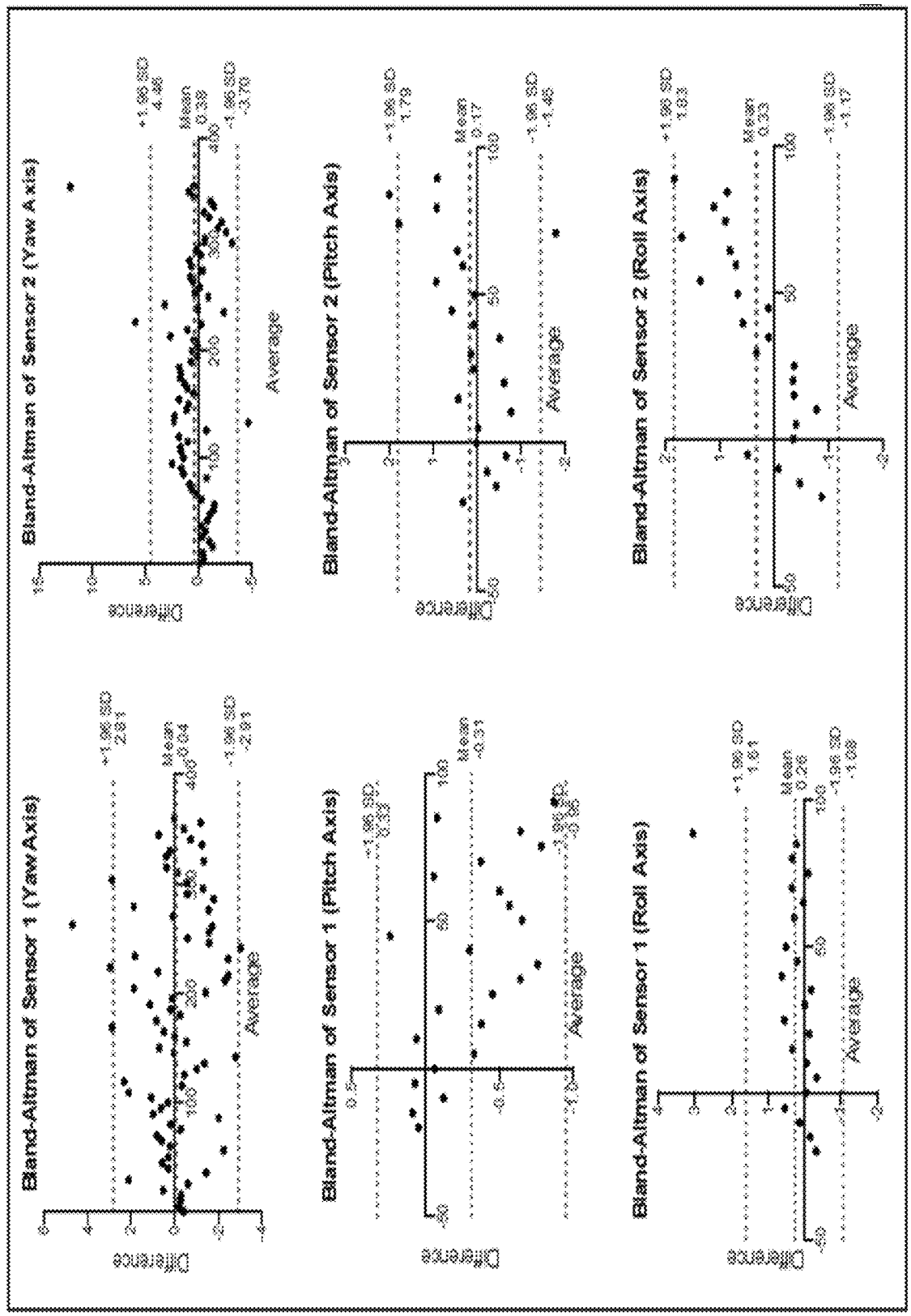

FIG. 12 shows agreement as assessed by the Pearson correlation coefficient and FIG. 13 shows the Bland-Altman plots for the same comparison.

FIG. 12 shows correlation between positional orientation measurements by the geared tripod head (x-axis) and the IMU sensor (y-axis). Plots were constructed for each of the yaw, pitch, and roll axes for both IMU sensors. Statistical significance for the correlation coefficient was set at $p < 0.05$. The correlation coefficient is shown overlaid for each comparison.

FIG. 13 shows are the Bland-Altman plots comparing IMU sensor measurement to the geared tripod head position. 95% limits of agreement are shown in each plot as a grey dotted line and the mean of the differences is shown as the red dotted line. The grey line is the 'the dotted line furthest from the x axis' and the red line is 'the dotted line closest to the x axis'

Overall, the sensor showed excellent agreement with the geared tripod head as shown both in the Pearson correlation coefficient analysis as well as the Bland-Altman analysis. The Pearson correlation coefficient for each comparison was very high (near one) with strong statistical significance ($p < 0.001$).

The Bland-Altman plots demonstrate no significant systemic bias in measurement with limits of agreement acceptable for use in this study. Concurrent validity has been established for the IMU sensors.

An experimental design was developed for objective comparison of the prototype camera system to the head-mounted GoPro. Two separate surgeons performed repeated skin procedures in a simulated operating room setting. The procedure performed was a z-plasty transposition flap on a porcine-based skin model.

The surgeon was outfitted with both the head-mounted GoPro and the shoulder-mounted prototype camera system simultaneously. The validated IMU sensors were affixed to each device. IMU sensor data logging as well as video capture were synchronized so that direct, time-matched comparisons could be made.

IMU sensor data was sampled at 10 Hz. Sensor data was in the form of quaternions and Euler angles. Euler angle displacement was calculated by taking the difference between subsequent Euler angle data points. The total angular displacement for the yaw, pitch and roll axes were calculated for each trial case.

These values were then divided by the case length to generate the average Euler angular displacement, in degrees per minute, for each axis. In a similar manner, rotation quaternions were calculated between subsequent quaternion data points (Equation 0-3).

This represents the rotation from one quaternion to the next along the shortest arc. The angle of the rotation quaternion in degrees was then calculated (Equation 0-4). The difference in quaternion rotation angles was calculated for each subsequent data point. The total angular displacement from the rotation quaternions was then calculated for each trial case.

This total value was then divided by the case length to generate the average quaternion angular displacement, in degrees per minute. The trial-specific Euler angular displacement and quaternion angular displacement were then averaged for overall values. Statistical analysis was performed. A paired two-sample t-test was used to compare mean angular displacement values for all of the included trials. An alpha of 0.05 was selected as the cut off for statistical significance. Results are presented as mean±standard deviation, unless otherwise specified.

$$qRot=qEnd*qStart.inversed(\ );$$

Equation 0-3: Calculating the Rotation Quaternion.
The rotation quaternion is calculated from two subsequent quaternions (qStart and qEnd)

$$rotAngle=2*a\ cos\ d(qRot(w));$$

Equation 0-4: Calculating the exact angle of rotation.
Where a cos d is the inverse cosine in degrees, qRot is the rotation quaternion calculated in Equation 0-3 and w is the scalar component of the quaternion representing the rotation around the vector component.

A total of 12 skin procedures were performed by two separate surgeons, amounting to 6 procedures per surgeon. The average procedure length was 9.2±1.7 minutes. IMU motion data was logged. Video data from both cameras was captured and coded according to camera type and trial number.

Figure 14:
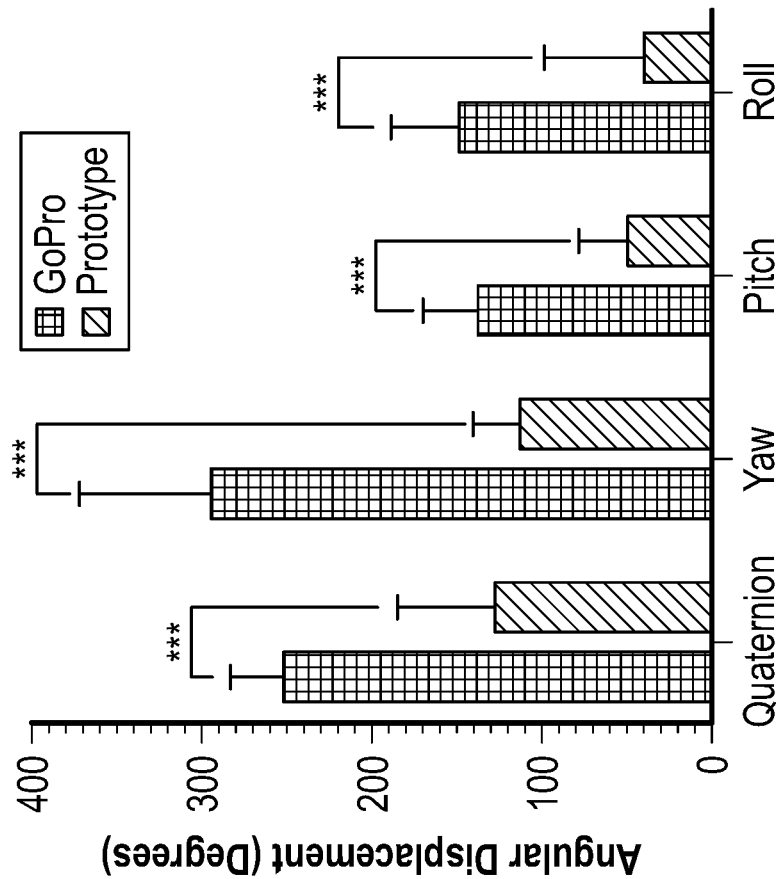
FIG. 14 includes on the left a photograph of the experimental setup, and on the right, plots of the average angular displacement, normalized for case length as degrees per minute, is shown on the Y-axis. Angular displacement was calculated from rotation quaternions as well as independently for each rotational axis represented by Euler angles, shown on the X-axis.
Figure 14:
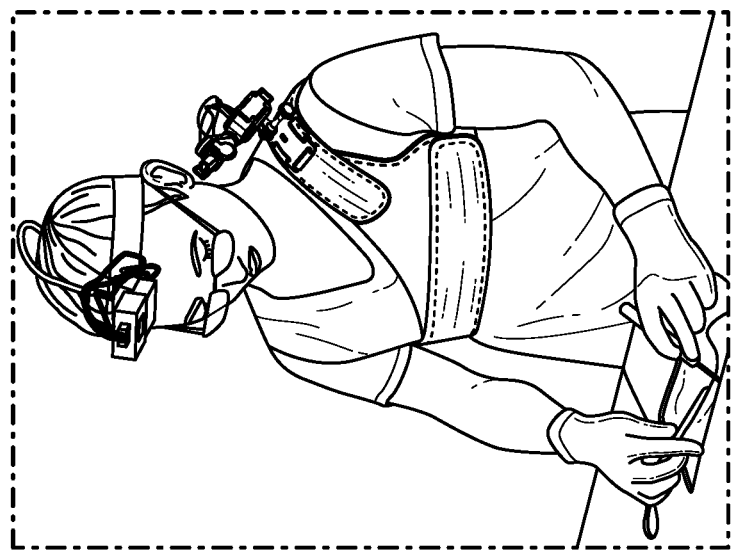

The prototype camera system demonstrated significantly less movement than the head-mounted GoPro when analyzed as quaternions (130±56 vs. 253±31, $p<0.001$) and as Euler angles (Yaw: 116±58 vs. 295±78, $p<0.001$, Pitch: 52±26 vs. 138±32, $p<0.001$, Roll: 43±26 vs. 149±40, $p<0.001$) (FIG. 14).

In FIG. 14: (Left) Shown is the experimental setup. (Right) The average angular displacement, normalized for case length as degrees per minute, is shown on the Y-axis. Angular displacement was calculated from rotation quaternions as well as independently for each rotational axis represented by Euler angles, shown on the X-axis.

Figure 15:
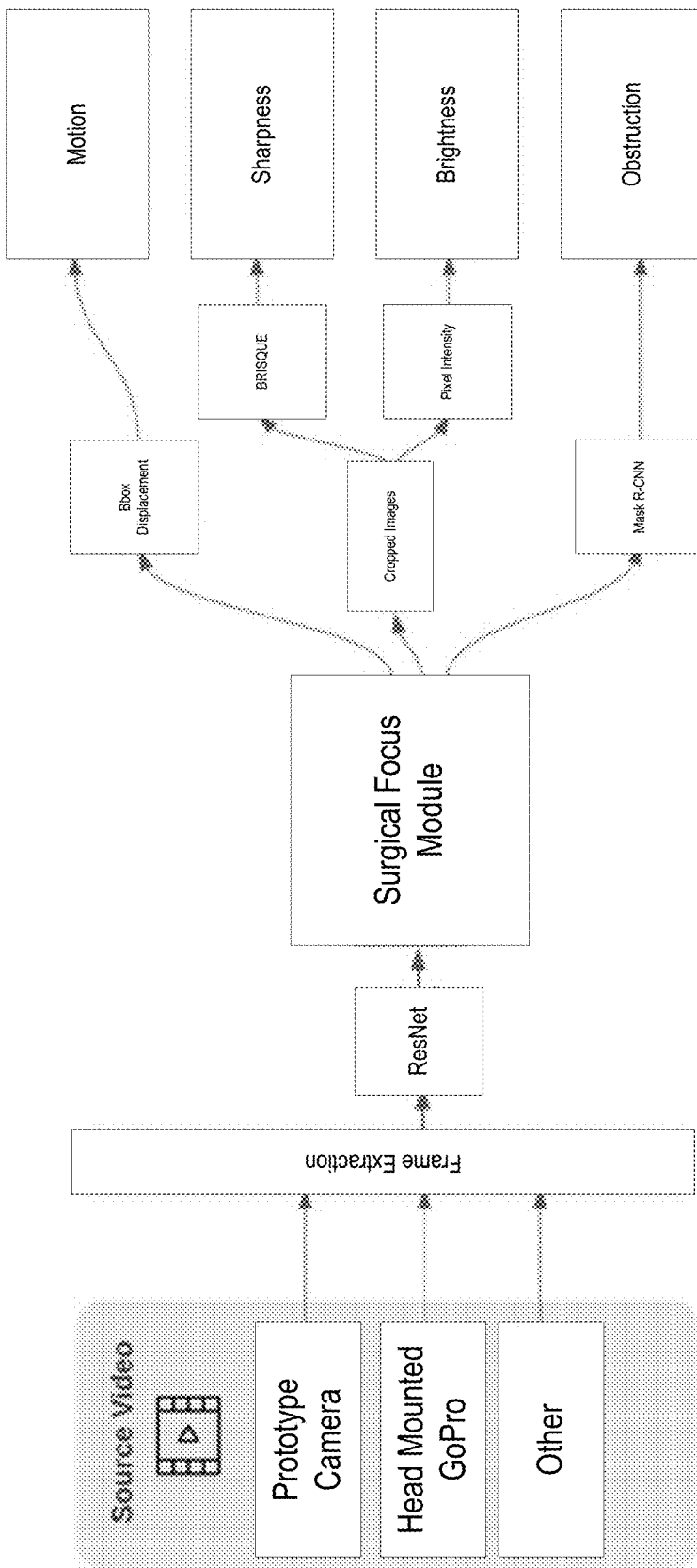
FIG. 15 is a block schematic of an example surgical focus mechanism, according to some embodiments.

FIG. 15 is a block schematic of an example surgical focus mechanism, according to some embodiments. The surgical focus mechanism can be a surgical focus module, trained using video data from various trials. In this example, the video data from simulation trials captured were algorithmically analyzed for objective, quantifiable comparison between the prototype camera system and the head-mounted GoPro.

The four outcome parameters evaluated were motion, sharpness, brightness/contrast, and obstruction of the surgical field. Source video files are converted to still frame sequences at a predefined sample rate. The still frame sequences are processed by the Surgical Focus Module. The outputs of the Surgical Focus Module are further analyzed to provide objective scores for each of the 4 target metrics: motion, sharpness, brightness/contrast and obstruction of the surgical field.

The source video files from both camera systems were comparable in terms of resolution (1920×1080 at 30 frames per second), compression (Quicktime H264 codec) and bitrate. The audio data was discarded. FFMPEG (FFmpeg Team, open source multimedia framework) was used to extract still frames at a rate of 1 frame per second in the Portable Network Graphic (PNG) format.

The surgical focus module was then used to process still frame sequences for each trial case. The surgical focus module was necessary for 2 main reasons. Firstly, it performed object detection and instance segmentation on key objects visible to the camera.

Once identified, mathematical and logical operations could be performed with these identified objects to assist in calculating the outcome metrics of interest.

Secondly, the surgical focus module could be used to crop video frames such that only the region of interest was analyzed. This was important because the raw video often contained significant noise in the periphery of each frame. For example, if an unprocessed video frame were to be analyzed for brightness, the center would likely be very bright and the periphery dark, and the brightness score would be affected by these two dichotomous regions. By cropping out only the area containing the surgical field, analyses can be performed only on the regions of interest.

The surgical focus module performs object recognition and instance segmentation on the still frame sequences provided. This is done, in an example embodiment using the CNN model (e.g., Mask R-CNN model), a deep learning framework for object detection and instance segmentation.

Convolutional Neural Networks (CNNs) are an useful architecture for most image recognition and classification. R-CNNs, with the 'R' standing for region, are an extension of CNNs that allow for object detection.

Figure 16:
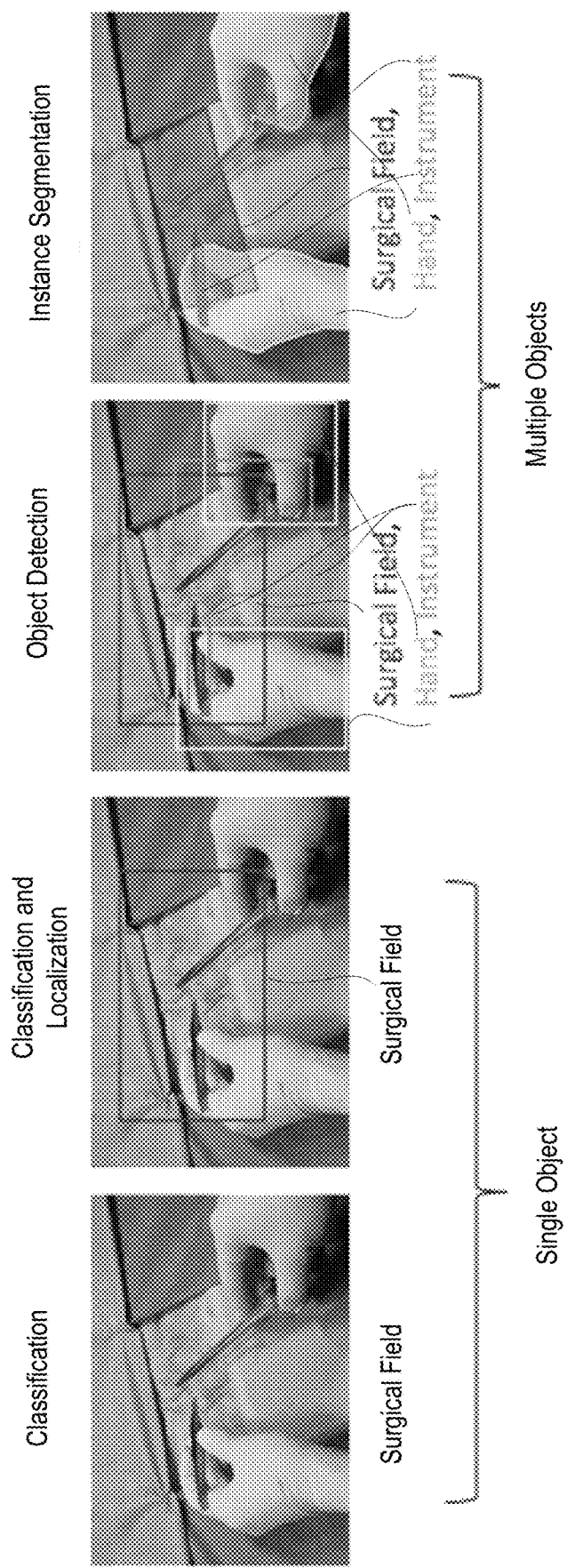
FIG. 16 shows image classification, object detection and instance segmentation examples.

A comparison of types of image classification tasks a model can perform is shown in FIG. 16. FIG. 16 shows image classification, object detection and instance segmentation examples.

While Mask-R-CNN is shown in various example embodiments herein, other CNNs are possible. Mask R-CNN is an extension of Faster R-CNN, which generates region proposals for the detections in the form of bounding boxes. Faster-RCNN is extended to Mask R-CNN by adding a branch to predict segmentation masks for each region of interest generated in Faster R-CNN. The additional branch for Mask-RCNN is a Fully Convolutional Network (FCN), which is applied to each region of interest to predict the segmentation mask for each pixel in that RoI.

The dataset used to train the model was developed from a combination of real and simulated surgical procedures. The real surgical procedures were from a previous project and consisted of minor skin surgical procedures captured with a high definition video camera.

The simulated surgical procedures were simple skin procedures performed on a porcine-skin model captured with both the head-mounted GoPro as well as the prototype camera. Still frames were extracted from the videos. A total of 528 training images and 133 validation images were used. The dataset was annotated using the online LabelBox platform (Labelbox, Inc).

Three classes were annotated: 1) Surgical Field, 2) Hand, and 3) Instrument. Annotations were in the form of polygon outlines of each object instance (FIG. 17).

Figure 17:
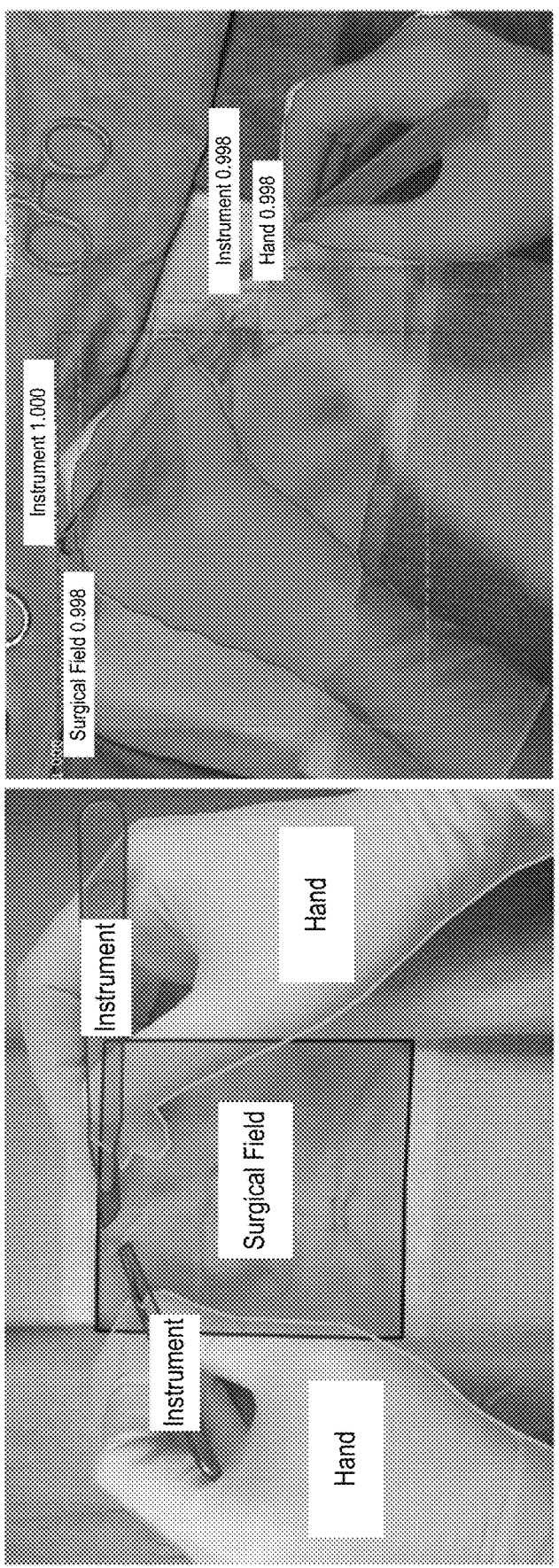
FIG. 17 shows image annotation and detection examples. (Left) Shown is an example of the annotated classes representing ground truth training data. (Right) Shown is an example of the model detection output.

In FIG. 17, image annotation and detection examples are shown. (Left) Shown is an example of the annotated classes representing ground truth training data. (Right) Shown is an example of the model detection output.

In this study, an end-to-end pre-trained Mask R-CNN model with a Resnet-101-FPN backbone was used. The model was pre-trained on the Common Objects in Context (COCO) dataset. By initializing training with the COCO weights, the principles of transfer learning were applied.

Transfer learning is a machine learning technique whereby knowledge from previously learned tasks is used to enhance learning of a similar, but different task. Transfer learning makes the learning process faster, more accurate and requires less training data. Learning hyperparameters were varied to try to optimize the model and learning progress was monitored using Tensorboard (FIG. 18).

Figure 18:
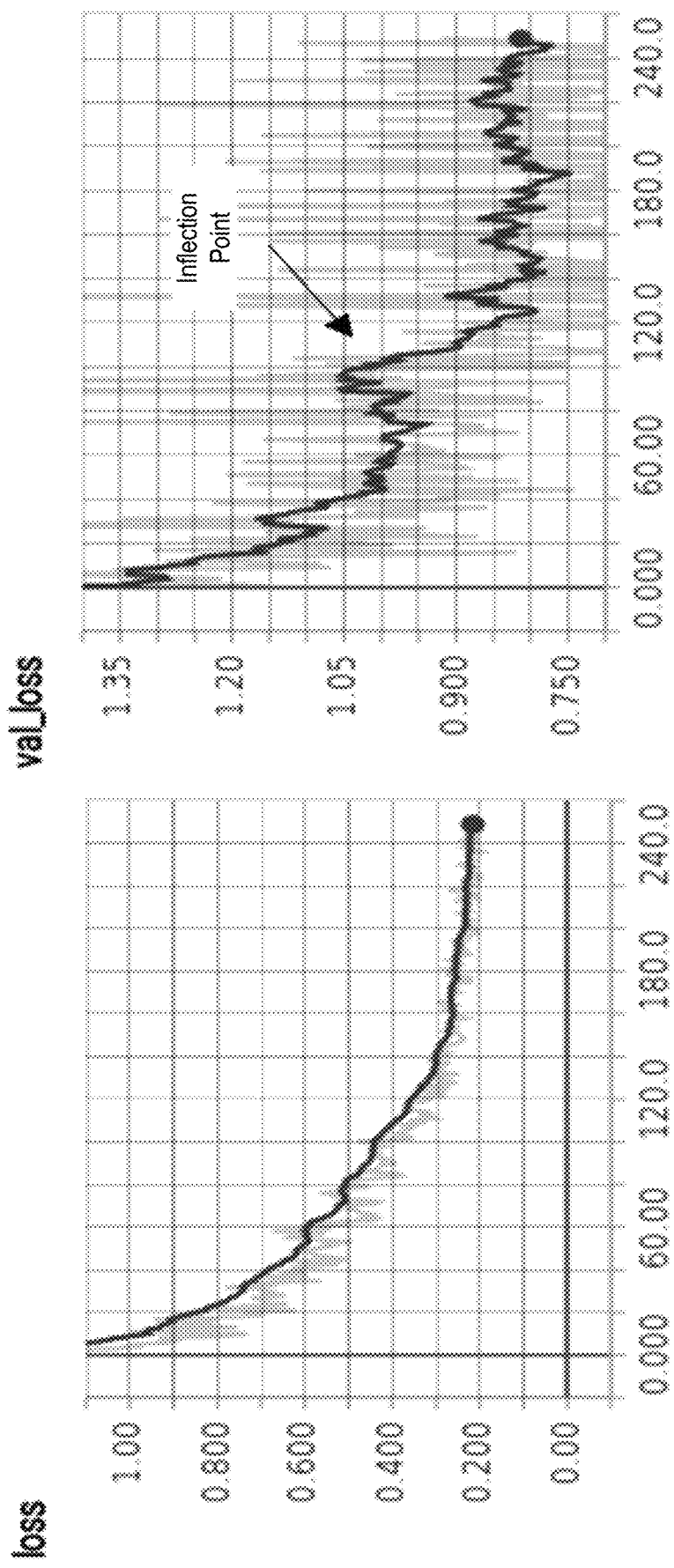
FIG. 18 shows Tensorboard training results of highest performing learning strategy. (Left) Shown is the training loss, which is the value of the cost function for the training data. (Right) Shown is the validation loss, which is the value of the cost function for the cross-validation data. Note the inflection point at epoch 100 (arrow, right) where the learning rate was decreased by a factor of 10.

FIG. 18 shows Tensorboard training results of highest performing learning strategy. (Left) Shown is the training loss, which is the value of the cost function for the training data. (Right) Shown is the validation loss, which is the value of the cost function for the cross-validation data. Note the inflection point at epoch 100 (arrow, right) where the learning rate was decreased by a factor of 10.

The hyper-parameters used in training the final model were: learning rate of 0.001 for the first 100 epochs, then 0.0001 for the remaining 150 epochs, with 100 steps per epoch, for a total of 250 epochs.

The remainder of the default Mask R-CNN training parameters were left unchanged.

The performance of the model was evaluated using precision and recall for the object detection task and Intersect Over Union (IOU) for the segmentation task.

The precision of an object classifier, also known as the positive predictive value, is defined as the ratio of true positives (TP) to the total number of predicted positives (TP+FP)(Equation 0-5).

$$Precision = \frac{TP}{TP+FP}$$

Equation 0-5: Precision Formula for Object Classification

The recall of an object classifier, also known as sensitivity, is defined as the ratio of TP to total ground truth positives (TP+FN)(Equation 0-6)

$$Recall = \frac{TP}{TP+FN}$$

Equation 0-6: Recall Formula for Object Classification

The Intersection over Union (IoU) score is a method for assessing the accuracy of an object detector on a particular dataset.

Using a predefined IOU threshold, bounding boxes predicted by an object detector can be compared to ground truth bounding boxes to determine whether the object detector's prediction is correct.

Figure 19:
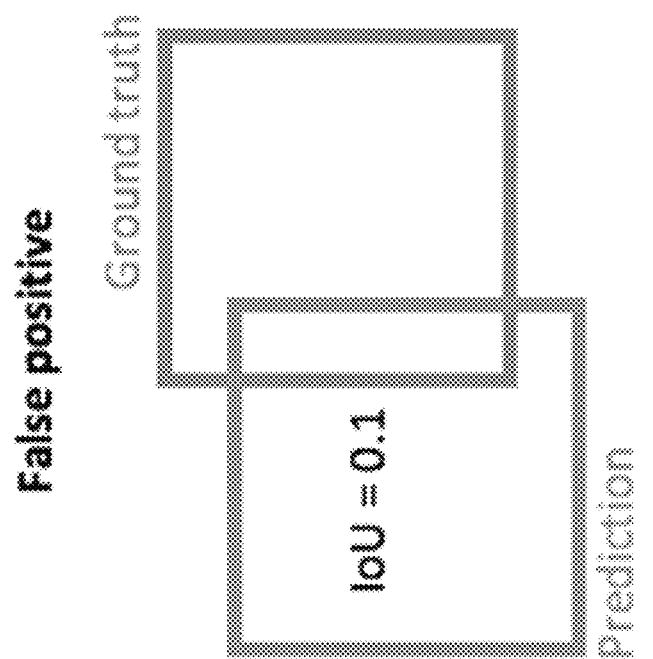
FIG. 19 is a diagram showing differences between true and false positives, according to some embodiments.
Figure 19:
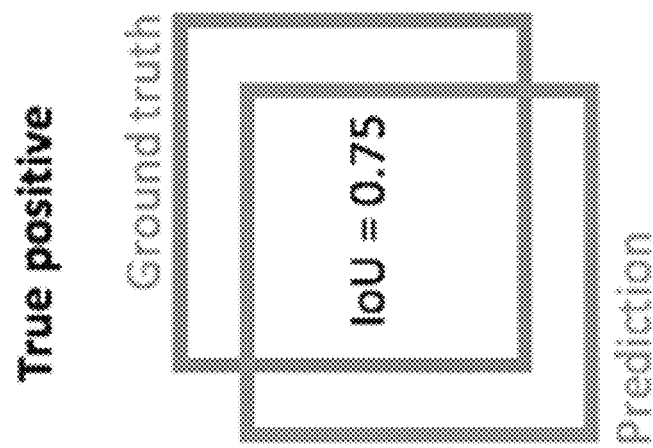

For example, in FIG. 19, at an IoU threshold of 0.5, panel A shows an acceptable prediction result that would be considered a true positive whereas panel B shows an unacceptable prediction result.

While the above example uses the IoU to categorize bounding box predictions based on ground truth data, the IoU principle can also be to quantify the percent overlap between predicted masks and ground truth masks. For this application, the IoU measures the number of pixels common between the ground truth and prediction masks divided by the total number of pixels present across both mass (FIG. 19).

$$IoU = (\text{ground truth mask} \cap \text{prediction mask})/(\text{ground truth mask} \cup \text{prediction mask})$$

Equation 3 7: Intersection over Union for evaluating image segmentation

Using the validation dataset, the abovementioned performance metrics of the model were determined. Precision and recall results were averaged for all detections and across all validation images at various IOU thresholds (Table 1). The average precision was then plotted against the varied IoU thresholds (FIG. 20).

Figure 20:
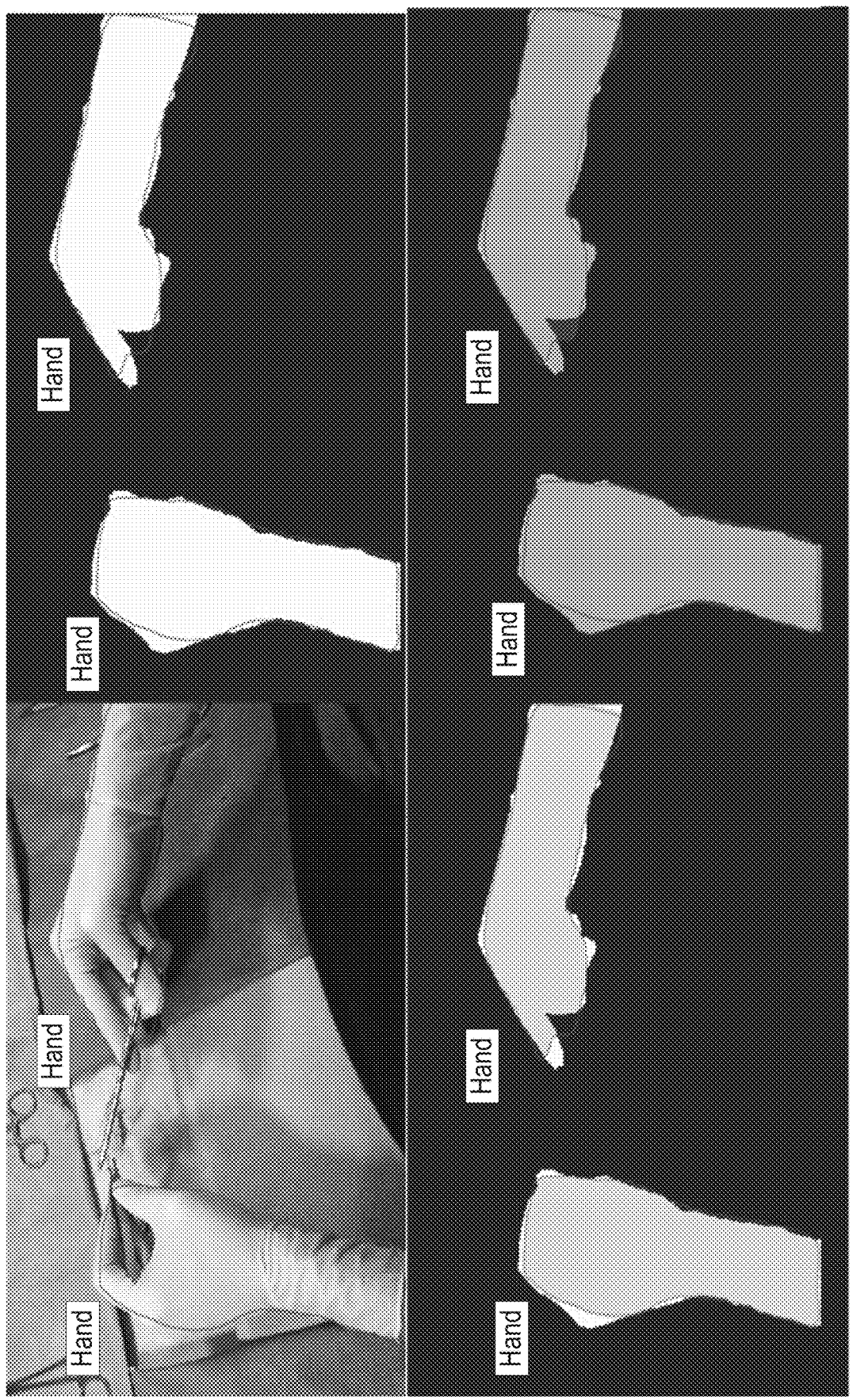
FIG. 20 shows an example intersection over Union for evaluating image segmentation. (Top Left) Shown is the predicted mask outline (red) for the Hand class. (Top Right) Shown is the ground truth mask (yellow) for the Hand class with the predicted mask outline (red) overlaid. (Bottom Left) Shown in green is the intersection between the ground truth mask and the predicted mask. (Bottom Right) Shown in orange is the union between the ground truth mask and the predicted mask. This specific example would have a high IoU value for the Hand class because the green area (intersection) divided by the orange area (union) would be close to 1.

FIG. 20 shows an example intersection over Union for evaluating image segmentation. (Top Left) Shown is the predicted mask outline (red) for the Hand class. (Top Right) Shown is the ground truth mask (yellow) for the Hand class with the predicted mask outline (red) overlaid. (Bottom Left) Shown in green is the intersection between the ground truth mask and the predicted mask. (Bottom Right) Shown in orange is the union between the ground truth mask and the predicted mask. This specific example would have a high IoU value for the Hand class because the green area (intersection) divided by the orange area (union) would be close to 1.

TABLE 1

Average Precision and Recall at various IoU Thresholds

| | IoU Thresholds | | | | | | | | | |
|---|---|---|---|---|---|---|---|---|---|---|
| | 0.5 | 0.55 | 0.6 | 0.65 | 0.7 | 0.75 | 0.80 | 0.85 | 0.9 | 0.95 |
| Precision | 0.8121 | 0.7769 | 0.7536 | 0.7096 | 0.6667 | 0.6158 | 0.5440 | 0.4045 | 0.2229 | 0.0207 |
| Recall | 0.8883 | 0.8684 | 0.8533 | 0.8410 | 0.7998 | 0.7543 | 0.6745 | 0.5139 | 0.3221 | 0.0993 |
| *AP@[0.5:0.05:0.95] | 0.5527 | | | | | | | | | |

*this represents the average precision averaged across all 10 IOU thresholds

The IoU was calculated for each class separately and averaged across all validation images. These were then combined to generate an overall IoU value for the model. Table 2 shows descriptive statistics for the IoU metrics obtained from the validation dataset.

Figure 21:
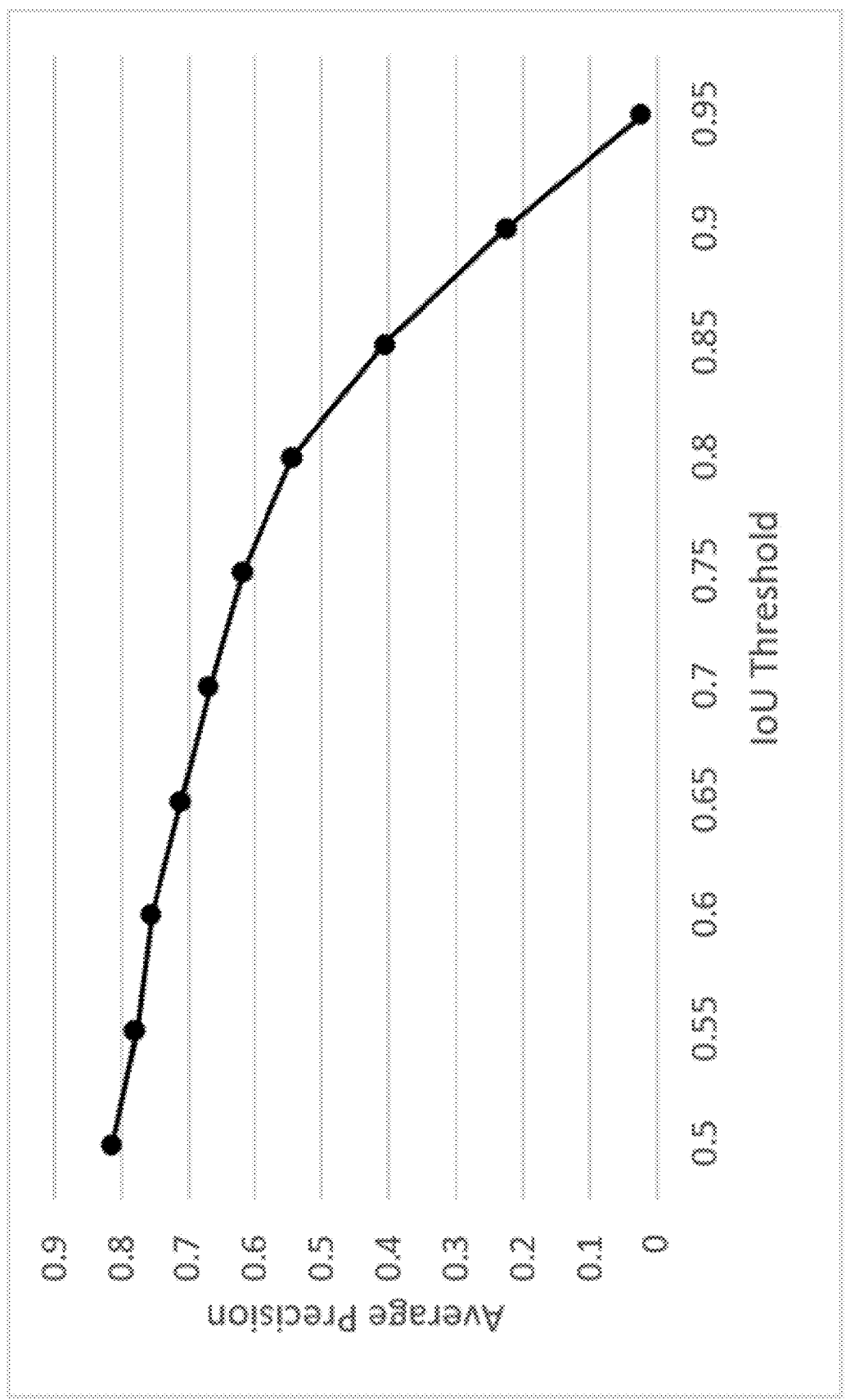
FIG. 21 shows average precision at varied IoU Thresholds.

FIG. 21 shows average precision at varied IoU Thresholds.

TABLE 2

Global and Class-specific IoU results

| | IoU Descriptive Statistics | | | | | |
|---|---|---|---|---|---|---|
| Class | Min | Q1 | Median | Q3 | Max | Range |
| Surgical Field | 0.000 | 0.7731 | 0.8743 | 0.9172 | 0.9683 | 0.9683 |
| Hand | 0.000 | 0.8413 | 0.8801 | 0.9070 | 0.9295 | 0.9295 |
| Instrument | 0.000 | 0.4251 | 0.6317 | 0.7084 | 0.8681 | 0.8681 |
| Overall | 0.000 | 0.6440 | 0.8228 | 0.8957 | 0.9683 | 0.9683 |

Figure 22:
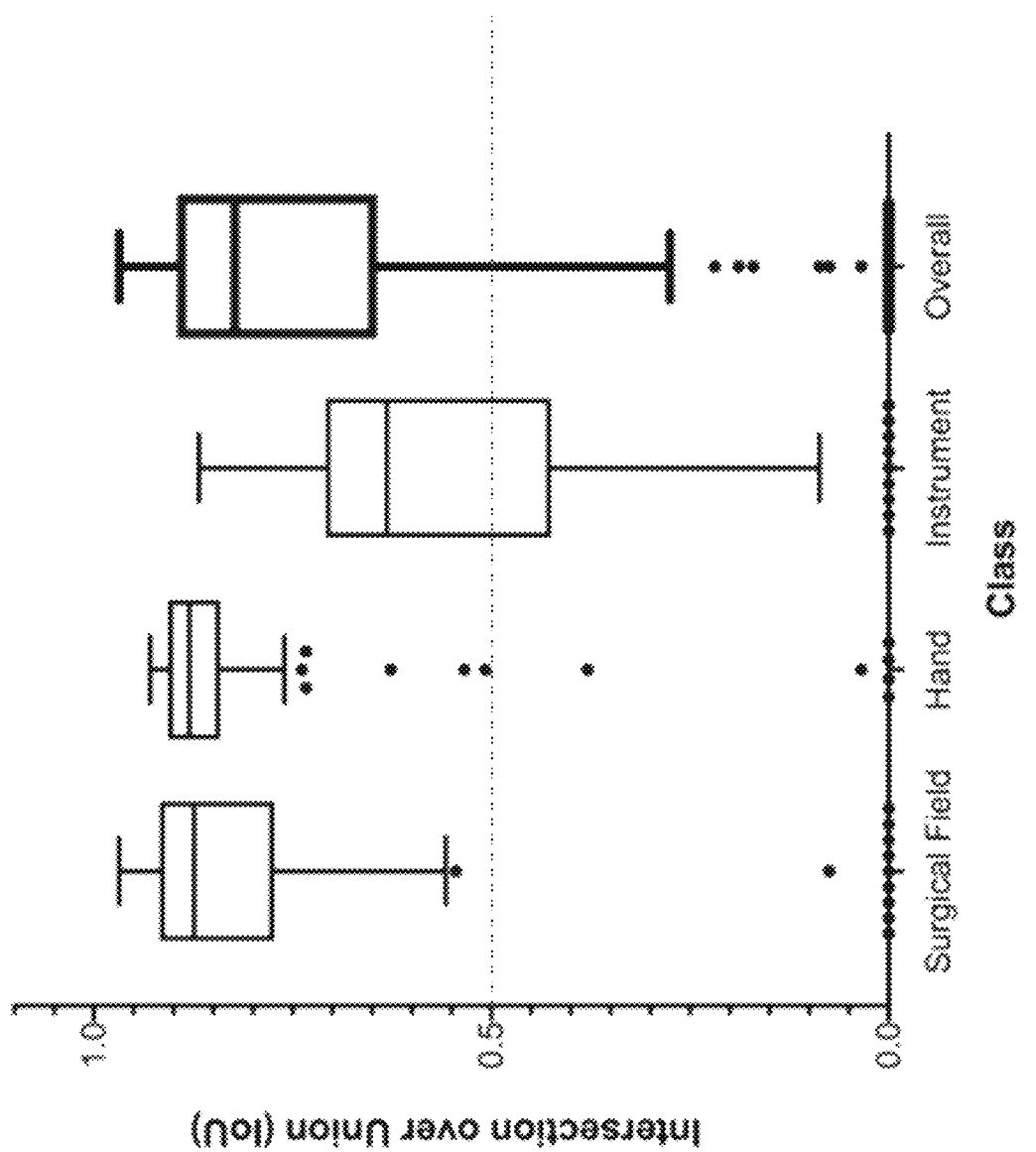
FIG. 22 is a Tukey Boxplot for Class-specific and Overall IoU values for validation images.

FIG. 22 is a Tukey Boxplot for Class-specific and Overall IoU values for validation images.

The box represents the lower (Q1) and upper (Q3) quartile, with the horizontal divider representing the median value. The whiskers represent values within 1.5 IQR and values outside this range are the dotted outliers. The dotted red line represents the IoU threshold for classifying a detection as a true positive (IoU threshold=0.5).

An additional motion metric derived from the video analysis was developed and assessed. This was done because many modern video cameras incorporate some degree of electronic or digital image stabilization. Using digital stabilization technology, the video footage from a jerky camera may still be quite stable. Because the video footage is the end-product of interest, it was important to include this additional motion metric in addition to the physical camera movement.

The video-based motion metric was determined using the displacement of the surgical field bounding box detected by the surgical focus module in adjacent video frames.

Because the operating table is fixed in position, any change in position of the surgical field from frame to frame can be attributed to movement of the camera.

Figure 23:
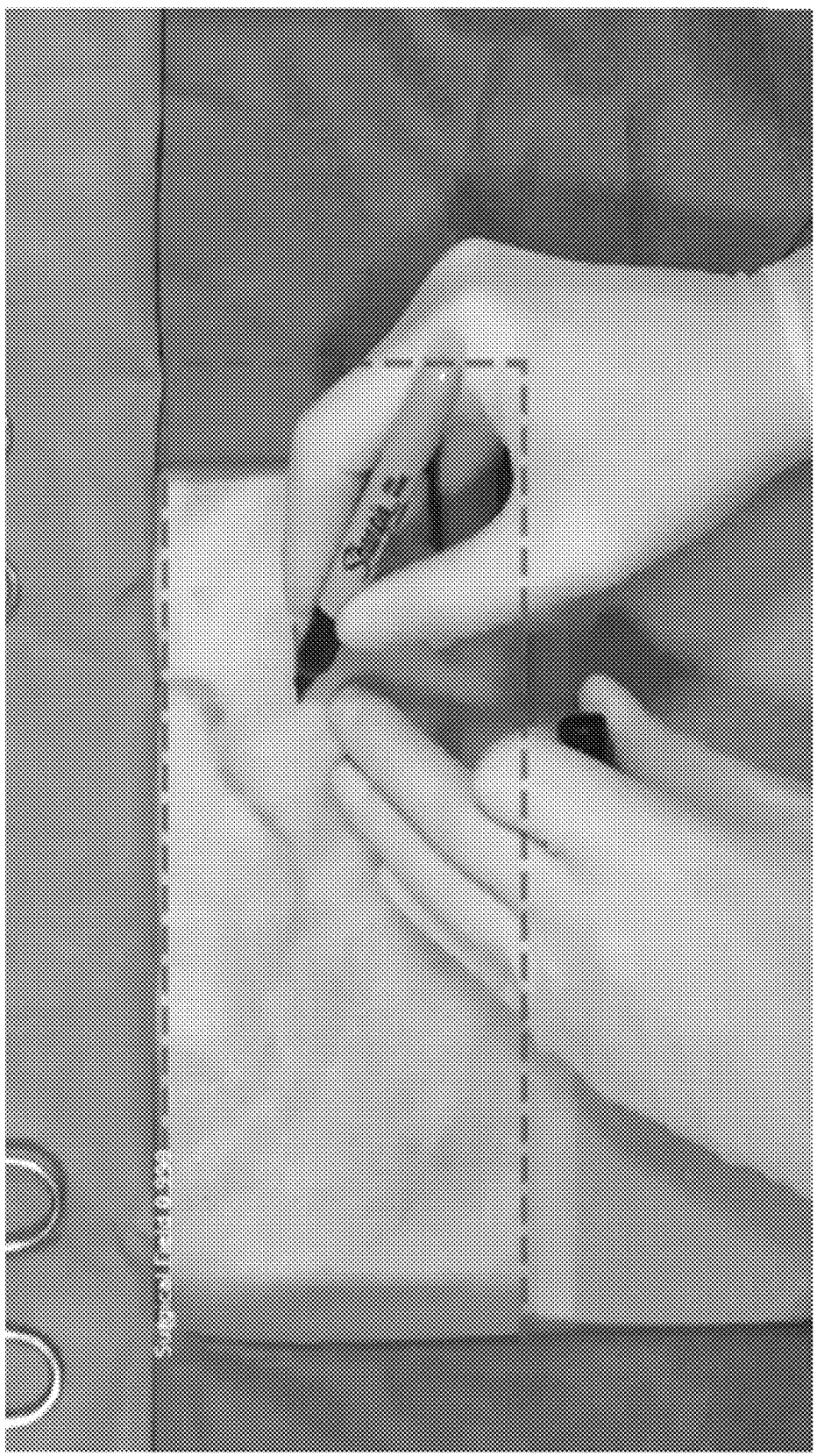
FIG. 23 shows raw video frames processed by the surgical focus module and where bounding boxes for the surgical field class were obtained.

Raw video frames were processed by the surgical focus module and bounding boxes for the surgical field class were obtained (FIG. 23).

A JSON (JavaScript Object Notation) file containing the coordinates of the bounding boxes for each frame was compiled. The JSON file was then analyzed using Matlab. The centre point of each surgical field bounding box was calculated and compared across adjacent frames.

Figure 24:
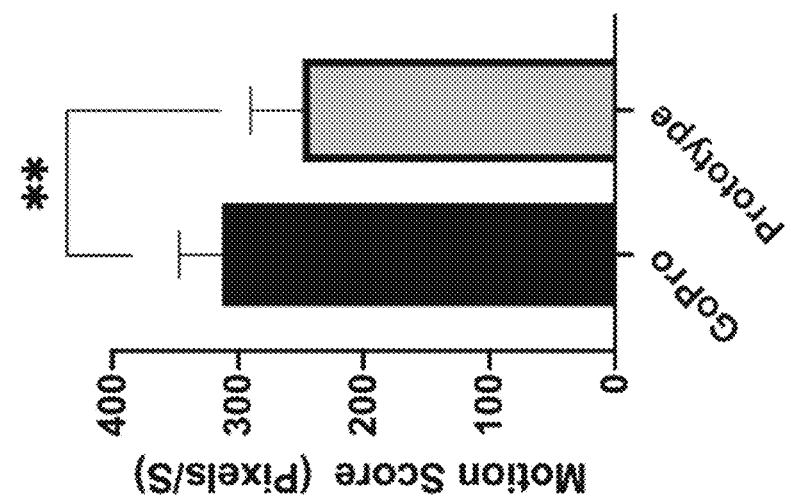
FIG. 24 is a diagram showing a vector representing the displacement of the bounding box centrepoint from one frame to the next overlaid on a photograph.
Figure 24:
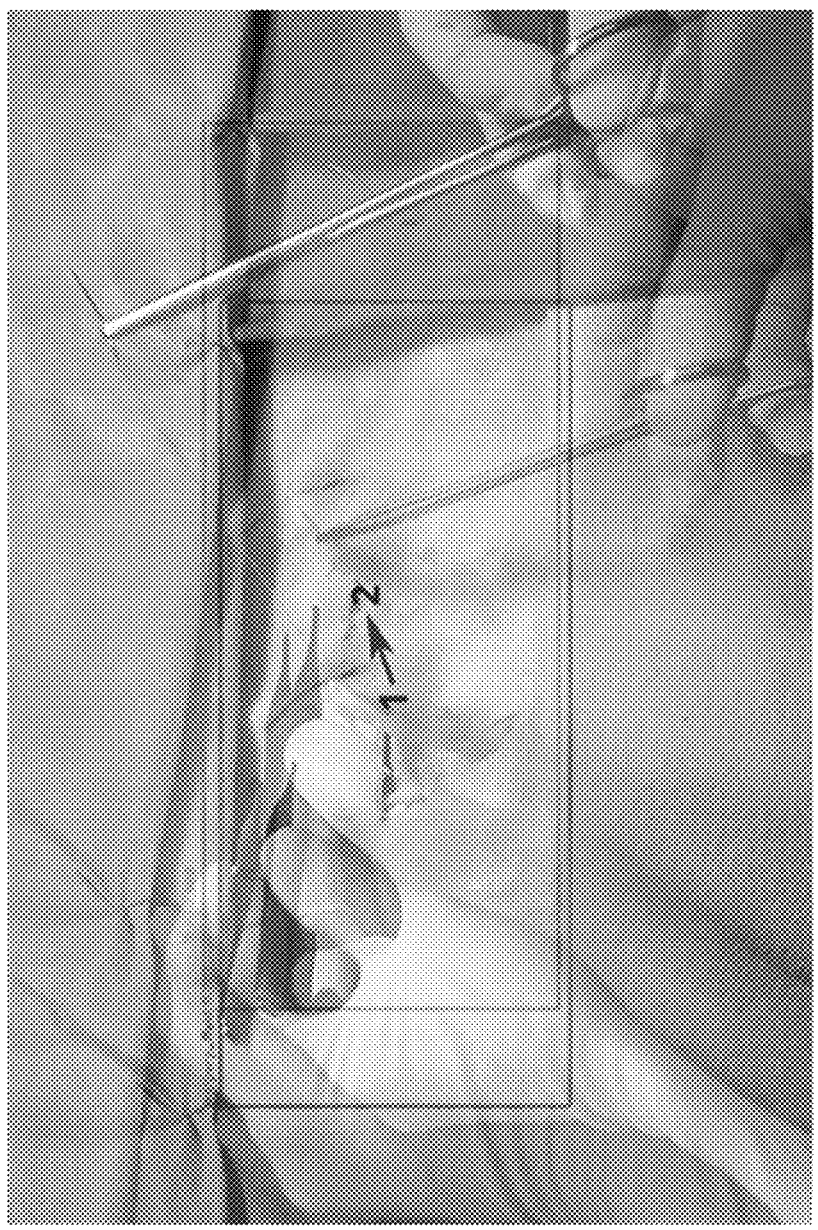

A vector representing the displacement of the bounding box centrepoint from one frame to the next was calculated (FIG. 24). Additional processing can be utilized to initiate control feedback using the displacement vector value. A 2D vector can be translated into 3D motor commands (e.g., Activate yaw motor by X amount, activate pitch motor by Y amount).

The 3D commands can also be utilized for generating verbal or textual (or graphical outputs) for a surgeon or practitioner to actuate, for example, by using a handle connected to an overhead light, moving of a camera module on a rolling stand, etc.

The verbal commands can include "please move the operating light to your left", the textual commands can relay the same on a heads up display or on a monitor, and the graphical commands can include visual graphical elements, such as rendered arrows or colored bars indicating movements requested to help center the visual region of interest over the object being tracked. As noted, the object being tracked can often move (e.g., perhaps the object being tracked is a bladder, which has been displaced to obtain access to various organs).

The magnitude of these displacement vectors can be totaled for an entire procedure and divided by the case length for each trial. This final value represented a normalized motion score represented as pixels per second.

A normalized motion score was calculated for both devices for all 12 trial cases. Results are presented as mean±standard deviation, unless otherwise specified. Statistical analysis was performed using a paired, two-sample t-test. Statistical significance was set at alpha=0.05.

The average motion score across all trials was significantly lower for the prototype camera system compared to the head-mounted GoPro (249.0±61.9 vs 312.8±51.6, p=0.0013, FIG. 22).

In FIG. 24, (Left) Shown are 2 adjacent frames that have been overlaid to demonstrate the change in bounding box position. Points 1 and 2 represent the centrepoints of the adjacent frames. The blue line connecting point 1 to point 2 represents the vector of displacement. (Right) Shown are the average motion scores for both devices.

Sharpness was assessed using the BRISQUE (Blind/Referencesless Image Spatial Quality Evaluator) score. The BRISQUE metric was selected because unlike many of the other image quality assessment metrics, which compute distortion specific features, the BRISQUE quantifies possible losses of 'naturalness' in the image leading to a more holistic measure of quality.

The BRISQUE metric was also accessible as it is available as a built-in Matlab function. The range of the BRISQUE score is from 0-100, where a lower score corresponds to a sharper image. Two sample images of simulated skin surgery, one blurrier than the other, with their respective BRISQUE scores labeled, are shown in FIG. 25.

Figure 25:
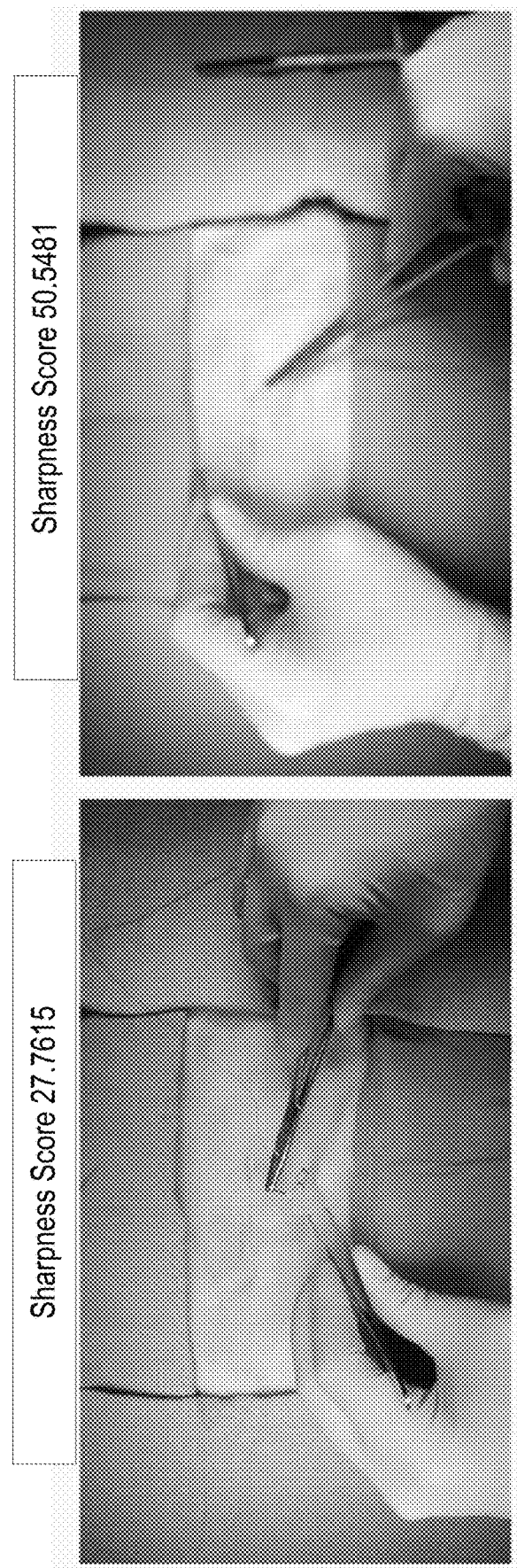
FIG. 25 is a sample BRISQUE calculation for two images.

FIG. 25: Sample BRISQUE calculation for two images. (Left) Sharper image, BRISQUE=27.8. (Right) Blurrier image, BRISQUE=50.5.

Still frames were extracted from source videos and processed using the surgical focus module. The surgical focus module calculated bounding boxes for the surgical field in each frame, and then cropped images were generated based on the dimensions of the bounding box plus a prespecified padding factor. In order to directly compare frames from both cameras, any frame pairs where a bounding box was not calculated because the algorithm missed it (false negatives), or there was no surgical field visible (true negatives) had to be discarded. This ensured that the image sequences from each camera remained synchronized and that frame comparisons between the two cameras referenced the same content.

Matlab was then used to read pairs of cropped images, one from each camera, and calculate the difference in BRISQUE score between the paired images. The BRISQUE score of the head-mounted GoPro was always subtracted from the prototype camera. This convention ensured that when the difference was calculated for each image pair, a negative value corresponded to the image from the prototype being sharper whereas a positive value corresponded to the image from the head-mounted GoPro being sharper.

Difference values were calculated for every frame pair and an array of difference values as well as the average difference value were exported for each of the 12 trials. The overall average difference value was then calculated. Results are presented as mean of differences with 95% confidence intervals, unless otherwise specified. Statistical analysis was performed using a one-sample t test for the difference in means. Statistical significance was set at alpha=0.05.

Figure 26:
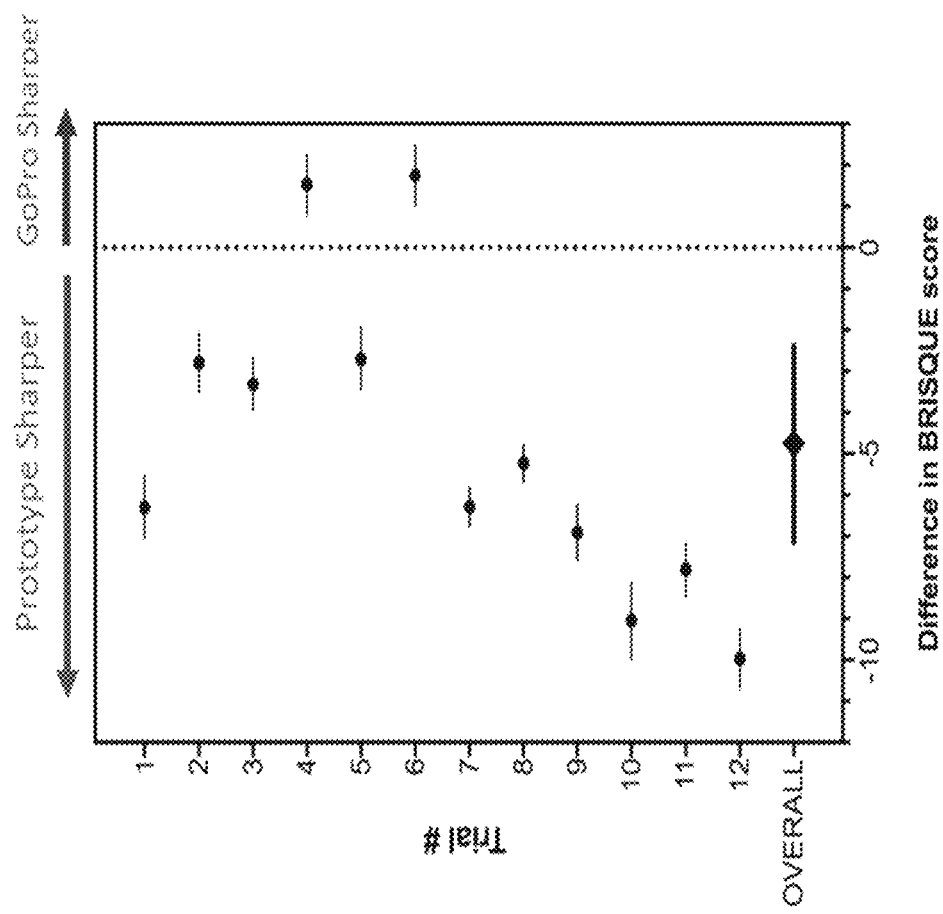
FIG. 26 is a plot that summarizes the trial-specific and overall results of the sharpness analysis.

The overall mean difference BRISQUE score averaged across all trials was −4.75 (95% C.I.: −7.15, −2.36, p=0.001) which suggests that the prototype camera, on average, produces sharper images. FIG. 26 summarizes the trial-specific and overall results of the sharpness analysis.

In FIG. 26, each row represents an individual trial, with the overall score in the last row. Dots represent the mean difference, with 95% confidence intervals of the mean. The vertical dotted line represents no difference. As indicated by the labels above the graph, values to the left of the 'no difference line' imply that the prototype produced a sharper image whereas values to the right of the 'no difference line' imply that the GoPro produced sharper images.

Brightness and contrast were assessed in Matlab. The brightness of an image can be represented mathematically as the mean pixel intensity and the contrast as the standard deviation in pixel intensity. The same synchronized cropped image pairs processed by the surgical focus module were used. Each pair of images was iteratively read by Matlab, converted to grayscale, and then mean pixel intensity and standard deviation in pixel intensity were calculated.

The same comparison convention was used, whereby the brightness and contrast scores from the head-mounted GoPro were always subtracted from the values calculated for the prototype camera. This meant that a positive difference in brightness corresponded to the prototype image being brighter and a positive difference in contrast corresponded to the prototype image having a higher contrast value.

Difference values were calculated for every frame pair and an array of difference values as well as the average difference value were exported for each of the 12 trials. Results are presented as mean of differences with 95% confidence intervals, unless otherwise specified. Statistical analysis was performed using a one-sample t test for the difference in means. Statistical significance was set at alpha=0.05.

The overall mean difference in brightness score was −1.21 (95% C.I.: −9.10, 6.69, p=0.74) and therefore was not significantly different for the prototype camera compared to the head-mounted GoPro. This implies that there is no significant difference in the brightness of the images produced by both cameras.

The overall mean difference in contrast score was 6.39 (95% C.I.: 4.72, 8.06, p<0.0001) and therefore the contrast score was significantly higher for the prototype camera compared to the head-mounted GoPro. This implies that the prototype camera, on average, produces higher contrast images.

Figure 27:
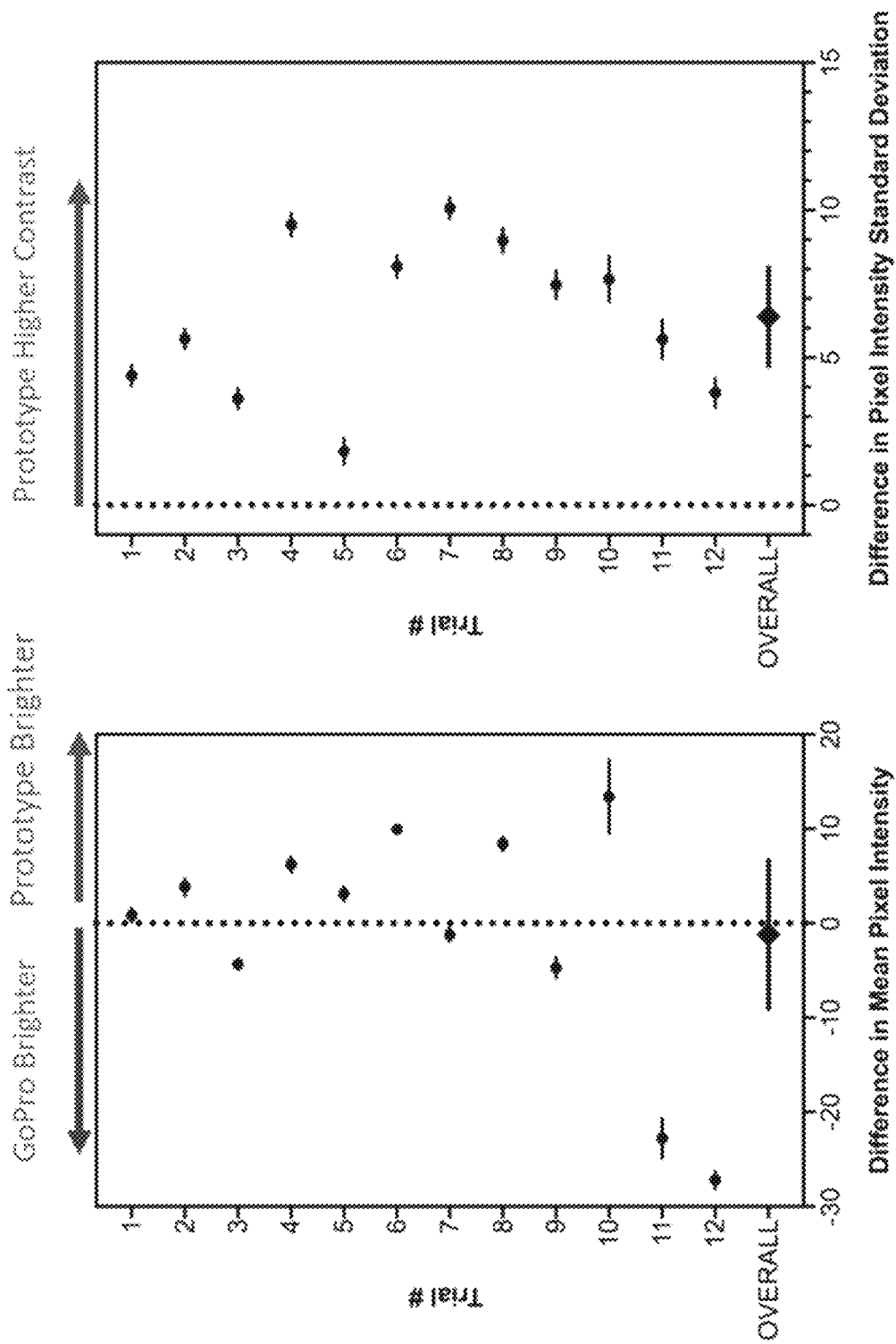
FIG. 27 is a plot that summarizes the trial-specific and overall results of the brightness and contrast analysis, shown as results of (Left) Brightness and (Right) Contrast Analysis.

FIG. 27 summarizes the trial-specific and overall results of the brightness and contrast analysis, shown as results of (Left) Brightness and (Right) Contrast Analysis.

Each row represents an individual trial, with the overall score in the last row. Dots represent the mean difference, with 95% confidence intervals of the mean. The vertical dotted line represents no difference. As indicated by the labels above the graph, values to the left of the 'no difference line' imply that the GoPro produced a brighter (left) or higher contrast (right) image whereas values to the right of the 'no difference line' imply that the prototype produced a brighter (left) or higher contrast (right) image.

Surgical field obstruction was defined as the percent of the area of the surgical field obstructed by either the surgeon's hands or instruments. The surgical focus module was used to perform instance segmentation to identify and outline the predefined classes: surgical field, hands, and instruments. The output of interest for this metric were the binary masks generated for each object.

A binary mask is a representation of an image where pixels corresponding to the masked area are coded as '1's and the remainder as '0's. The 'hand' and 'instrument' classes were combined such that a single mask containing all instances of these classes was generated. This was termed the 'obstruction mask'. A second mask was generated for the 'surgical field' class. The masks could then be compared using a logical 'AND' operation. This would identify any pixels which belong to both the surgical field and the obstruction masks.

Figure 28:
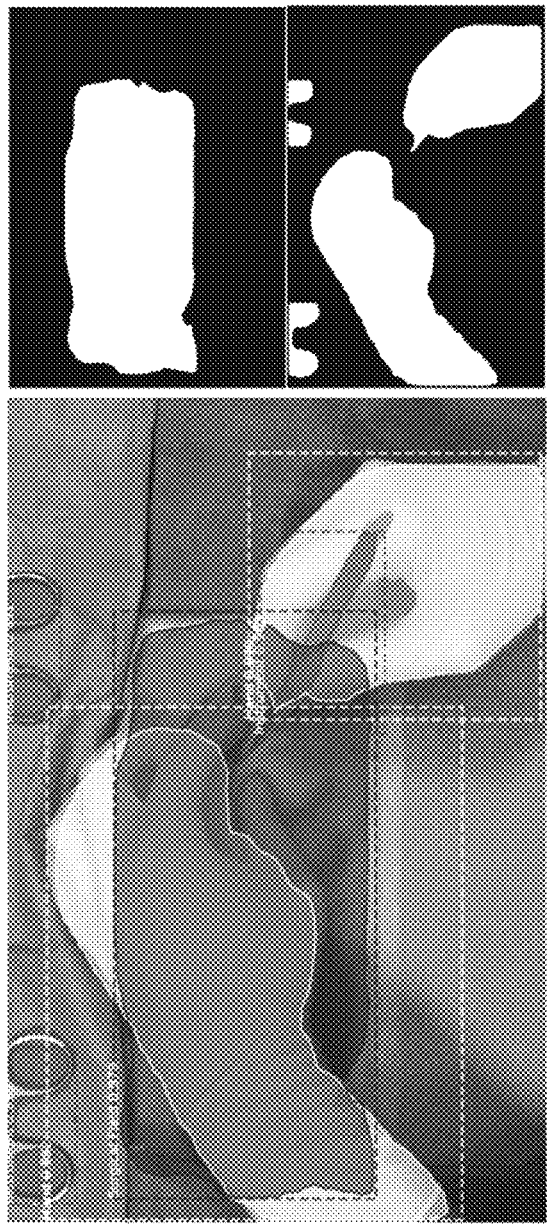
FIG. 28 is a surgical field obstruction example: (Top Left) Shown are the instance segmentation detection results. (Top Right) Shown is the extracted surgical field mask (upper) and obstruction mask (lower). (Bottom) Shown is the result of the comparison between the surgical field and obstruction masks, where the pink area divided by the yellow area represents the present of surgical field obstructed.
Figure 28:
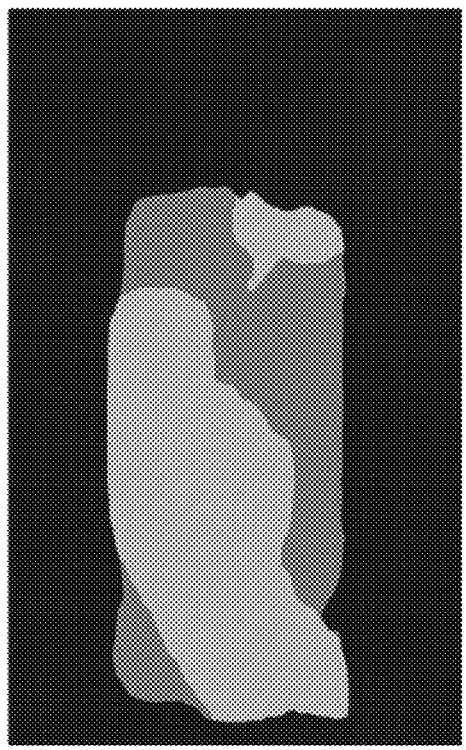

The sum of these overlapping pixels divided by the total number of pixels identified in the surgical field mask represents the percent obstruction of the surgical field in any given frame (FIG. 28).

The obstruction score can be tracked and maintained in a data structure as a proxy indicator of quality of camera view. This would be relevant if, for example, there was multi-camera setup where multiple cameras from different vantage points were all pointing at the same surgical field. When the recording camera developed a poorer view, e.g., due to excessive obstruction, this would trigger a switch to one of the other cameras that had the least obstruction, as measured by the algorithm. This could be relevant for either on-the-fly assembly of an optimal video stream, or all the cameras could be running simultaneously and the algorithm would run afterwards to assemble an optimal video feed and thus reduce the storage needs from multiple cameras and remove the manual work that would be required to go through all the feeds and manually select the best views.

Accordingly, in some embodiments, there are two or more cameras that are focusing in on the visual region of interest in different angles. In this example, both cameras can be different cameras placed on the shoulders of a surgeon and a physician's assistant, respectively. Each are conducting different tasks—the assistant is aiding in the provisioning of tools and suturing, while the surgeon is operating on the main object. A third camera is an overhead camera that is in a fixed orientation. Each of these cameras can either have their own processor units conducting segmentation mask analysis, or can be coupled to a shared processor processing video outputs.

The amount of obstruction can be tracked for each camera, and the different feeds, when recorded together, can each have different metadata associated with them across different time durations of the procedure. The procedure can be segmented into different time or sub-sections, such as an preparation section, opening of the individual, different stages of the surgery, the closing of the individual, and post-operative cleanup. The quality scores of each recording device can be utilized to determine which angle or perspective should be emphasized for each segment corresponding to various sections or subsections of the procedure, which could then be utilized to determine which parts of each output should be retained as a record or which outputs should be transmitted (e.g., if there are limited networking resources available or limited bandwidth).

FIG. 28 is a surgical field obstruction example: (Top Left) Shown are the instance segmentation detection results. (Top Right) Shown is the extracted surgical field mask (upper) and obstruction mask (lower). (Bottom) Shown is the result of the comparison between the surgical field and obstruction masks, where the pink area divided by the yellow area represents the present of surgical field obstructed.

The percent of surgical field obstructed was determined by the processor for every frame pair in the image sequence. Comparisons were made between paired frames, where one image was captured from the prototype and the other from the head-mounted GoPro. Any pairs of frames where the surgical field was present but not detected by the surgical focus module (i.e., false negatives) were discarded.

True negatives (i.e., where there was no surgical field in view) were treated as 100% obstruction of the surgical field. The difference in percent obstructed was calculated for each frame pair by subtracting the GoPro value from the prototype value.

This convention meant that a positive difference value corresponded to the Prototype view being more obstructed whereas a negative difference value corresponded to the GoPro view being more obstructed. Difference values were calculated for every frame pair and an array of difference values as well as the average difference value were exported for each of the 12 trials. Results are presented as mean of differences with 95% confidence intervals, unless otherwise specified. Statistical analysis was performed using a one-sample t test for the difference in means. Statistical significance was set at alpha=0.05.

The overall mean difference in percentage of the surgical field obstructed was 5.12 (95% C.I.: 3.76, 6.49, p<0.0001)

and therefore surgical field obstruction was significantly higher for the prototype camera compared to the head-mounted GoPro.

Figure 29:
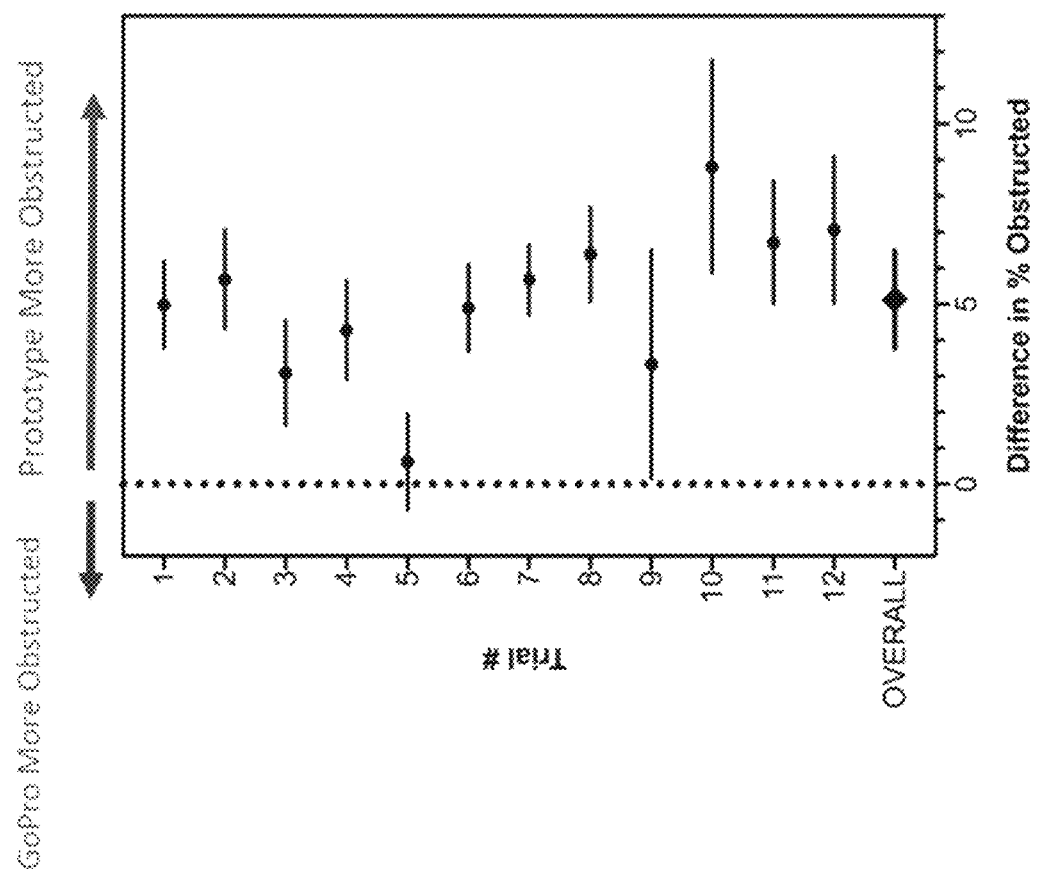
FIG. 29 summarizes the trial-specific and overall results of the obstruction analysis.

FIG. 29 summarizes the trial-specific and overall results of the obstruction analysis. In FIG. 29, each row represents an individual trial, with the overall score in the last row. Dots represent the mean difference, with 95% confidence intervals of the mean. The vertical dotted line represents no difference. As indicated by the labels above the graph, values to the left of the 'no difference line' imply that the GoPro produced images with higher surgical field obstruction whereas values to the right of the 'no difference line' imply that the prototype camera produced images with higher surgical field obstruction.

Objective comparison of the two camera devices consisted of one physical motion metric, captured by an IMU sensor, as well as four algorithmic assessments performed on the video files recorded. The physical sensor demonstrated less movement of the prototype camera compared to the head mounted GoPro. When the video data was analyzed, the prototype demonstrated less video frame motion, a sharper image, with higher contrast, but with more surgical field obstruction than the head-mounted GoPro.

The decreased motion of the prototype camera as compared to the head-mounted GoPro, both in physical camera motion and video frame movement, was an expected finding. This was because during the course of an operation, the shoulder exhibits less movement than the head. Furthermore, the addition of the gimbal stabilizer was expected to reduce movement further by detecting and correcting for the surgeon's movements in real time. Sharpness and brightness were expected to be fairly similar between the two devices, as no major modifications targeting these parameters were made.

The increased motion of the head-mounted GoPro, however, could have contributed to a poorer sharpness score due to motion blur artifact. Furthermore, in the simulated OR setting, the head-mounted GoPro had a narrower field of view than the prototype camera.

This means that when the same frame was directly compared to the prototype camera, the image from the head-mounted GoPro would contain a higher proportion of skin. This uniformly bright area of skin would therefore result in a diminished contrast range and this may be one reason there were higher contrast scores for the prototype camera. Finally, the higher degree of obstruction seen with the prototype camera was also expected because of the change from the head-mounted to the shoulder-mounted position.

As the perspective of the camera changes from a more top-down view to an angled or side view, foreground objects such as hands or instruments will obscure a greater proportion of the background surgical field. While a camera positioned close to and angled coaxial to the Surgeon's eyes would theoretically provide the best vantage point, the small trade off in increased obstruction for all the issues with a head-mounted camera seems reasonable.

It is also important to recognize that the 5.12% increased obstruction observed with the prototype device may not even be apparent to the viewer, and that subjective correlation would be important. The importance of developing a quantifiable obstruction metric, however, is that it allows objective comparison of any number of future devices, which may have much more or less degrees of surgical field obstruction.

Inaccuracies due to fluctuating sizes of the detected regions could potentially be remedied by incorporating looking-ahead or looking-back averaging, where the area of the detected surgical field is averaged over a few frames for a more representative value. Furthermore, any changes that lead to more accurate detection and masking would improve the accuracy of calculations. For example, changing the surgeon's gloves to a higher contrast colour may facilitate more accurate detection by the algorithm. Finally, the addition if additional training data would likely improve the algorithm resulting in more accurate detection and masking, and ultimately more accurate measurements. It would also be interesting to remove COCO classes that one would not expect to see in the target domain, the operating room, such as bikes or dogs and keep objects that may be similar (e.g., rectilinear objects such as cars) and then observe how this affects the transfer learning process.

While the motion and obstruction metrics were designed specifically for assessing the surgical setting, the sharpness and brightness/contrast metrics were not application-specific. The BRISQUE score is a general, referenceless quality evaluator and the brightness/contrast metric was based on pixel intensity calculations. A potentially more robust and application-specific approach to these metrics would be to generate additional deep learning algorithms.

This could be done by artificially creating blur artifact and adjusting brightness and contrast at set levels in the same surgical training images, thus creating new datasets. A classifier could then be trained on these new datasets specifically for each metric.

In conclusion, an application-specific framework was developed to objectively evaluate a camera device as well as the quality of the video it produces, and this was then used to compare the prototype camera system to the head-mounted GoPro.

The foregoing discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

Although the embodiments have been described in detail, it should be understood that various changes, substitutions and alterations can be made herein.

Moreover, the scope of the present application is not intended to be limited to the particular embodiments of the process, machine, manufacture, composition of matter, means, methods and steps described in the specification.

As can be understood, the examples described above and illustrated are intended to be exemplary only.

What is claimed is:

1. A recording device for generating one or more recordings of a surgical procedure, the recording device comprising:
    an imaging sensor residing within a housing;
    a computer processor coupled with computer memory, the computer processor configured to:
        receive a stream of image frames from the imaging sensor;
        continuously identify, using a trained machine learning data model architecture processing the stream of image frames, a visual region of interest within a field of view of the imaging sensor from the stream of image frames, the visual region of interest based on tracking a physical object relating to the surgical procedure in the field of view, the visual region of interest including a centroid;
        generate a displacement vector data structure when the centroid of the visual region of interest has been displaced between temporally proximate frames of the stream of image frames, the displacement vector data structure representative of a directional shift; and
        generate a control signal requesting movement of the imaging sensor or the housing in a direction based at least on the displacement vector data structure.

2. The recording device of claim 1, wherein the trained machine learning data model architecture is a Convolutional Neural Network (CNN) that is adapted for detection of the object and instance segmentation.

3. The recording device of claim 2, wherein the CNN is adapted to predict, for each pixel of an image frame of the stream of frames, a corresponding segmentation mask selected from a plurality of potential segmentation masks, and wherein the visual region of interest is derived at least from the associated segmentation mask corresponding to each pixel.

4. The recording device of claim 3, wherein the plurality of potential segmentation masks includes a first segmentation mask tracking the physical object relating to the surgical procedure in the field of view and one or more additional segmentation masks tracking one or more corresponding obstructions;
    wherein the CNN is adapted to utilize the first segmentation mask and the one or more additional segmentation masks together to identify an overall obstruction amount for a particular frame of the stream of frames; and
    wherein the processor is further configured to annotate the stream of image frames with additional metadata indicative of the overall obstruction amount for each frame of the stream of image frames.

5. The recording device of claim 2, wherein the CNN is pre-trained on a large scale object detection, segmentation, and captioning data set such that the CNN is initialized with weights derived from the pre-training to apply transfer learning where training on previously learned tasks is used to enhance learning of a similar but different task.

6. The recording device of claim 4, wherein training parameters for the CNN include a decreasing stepwise learning rate as training progresses through staged epochs.

7. The recording device of claim 1, wherein the visual region of interest is used to crop the stream of image frames, and wherein the computer processor is further configured to store a cropped stream of image frames onto a data storage.

8. The recording device of claim 1, wherein the housing is mounted on or positioned proximate to an individual's shoulder;
    wherein the housing is coupled with a gimbal having actuators thereon for controlling a gimbal roll axis, a gimbal pitch axis and a gimbal yaw axis; and
    wherein the displacement vector data structure is transformed into a corrective gimbal actuator command for physically repositioning of the imaging sensor or the housing.

9. The recording device of claim 1, wherein the control signal is converted into a user interface output requesting an individual physically reposition the imaging sensor or the housing in accordance with the displacement vector data structure representative of the directional shift.

10. The recording device of claim 1, wherein the recording device is mounted into or positioned proximate to a repositionable overhead light.

11. The recording device of claim 1, wherein the housing is a wearable harness.

12. The recording device of claim 11, wherein the wearable harness is mounted on a body of a person, and the recording device is coupled to a mountable on the housing such that the recording device is positioned on a shoulder of the person, the wearable harness adapted to be worn on top of a sterile surgical gown.

13. The recording device of claim 1, wherein the housing is mountable onto a fixed mounting point.

14. The recording device of claim 1, wherein the housing is mountable onto a fixed track such that the housing is conveyable across an axis provided by the fixed track through operation of a motor coupled to the fixed track.

15. A method for generating one or more recordings of a surgical procedure using an imaging sensor residing within a housing, the method comprising:
    receiving a stream of image frames from the imaging sensor;
    continuously identifying, using a trained machine learning data model architecture processing the stream of image frames, a visual region of interest within a field of view of the imaging sensor from the stream of image frames, the visual region of interest based on tracking a physical object relating to the surgical procedure in the field of view, the visual region of interest including a centroid;

generating a displacement vector data structure when the centroid of the visual region of interest has been displaced between temporally proximate frames of the stream of image frames, the displacement vector data structure representative of a directional shift; and generating a control signal requesting movement of the imaging sensor or the housing in a direction based at least on the displacement vector data structure.

16. The method of claim 15, wherein the trained machine learning data model architecture is a Mask Region-based Convolutional Neural Network (R-CNN) that is adapted for detection of the object and instance segmentation;

wherein the Mask R-CNN is adapted to predict, for each pixel of an image frame of the stream of frames, a corresponding segmentation mask selected from a plurality of potential segmentation masks, and wherein the visual region of interest is derived at least from the associated segmentation mask corresponding to each pixel, wherein the plurality of potential segmentation masks includes a first segmentation mask tracking the physical object relating to the surgical procedure in the field of view and one or more additional segmentation masks tracking one or more corresponding obstructions; and wherein the Mask R-CNN is adapted to utilize the first segmentation mask and the one or more additional segmentation masks together to identify an overall obstruction amount for a particular frame of the stream of frames; and the method further comprises:

annotating the stream of image frames with additional metadata indicative of the overall obstruction amount for each frame of the stream of image frames.

17. The method of claim 16, wherein the Mask R-CNN is pre-trained on a large scale object detection, segmentation, and captioning data set such that the Mask R-CNN is initialized with weights derived from the pre-training to apply transfer learning where training on previously learned tasks is used to enhance learning of a similar but different task.

18. The method of claim 15, wherein the housing is mounted on or positioned proximate to an individual's shoulder;

wherein the housing is coupled with a gimbal having actuators thereon for controlling a gimbal roll axis, a gimbal pitch axis and a gimbal yaw axis; and wherein the displacement vector data structure is transformed into a corrective gimbal actuator command for physically repositioning the imaging sensor or the housing.

19. The method of claim 15, wherein the control signal is converted into a user interface output requesting an individual physically reposition the imaging sensor or the housing in accordance with the displacement vector data structure representative of the directional shift.

20. A non-transitory computer readable medium storing machine interpretable instructions, which when executed by a processor, cause the processor to perform a method for generating one or more recordings of a surgical procedure using an imaging sensor residing within a housing, the method comprising:

receiving a stream of image frames from the imaging sensor;

continuously identifying, using a trained machine learning data model architecture processing the stream of image frames, a visual region of interest within a field of view of the imaging sensor from the stream of image frames, the visual region of interest based on tracking a physical object relating to the surgical procedure in the field of view, the visual region of interest including a centroid;

generating a displacement vector data structure when the centroid of the visual region of interest has been displaced between temporally proximate frames of the stream of image frames, the displacement vector data structure representative of a directional shift; and generating a control signal requesting movement of the imaging sensor or the housing in a direction based at least on the displacement vector data structure.

* * * * *